(12) United States Patent
Emili et al.

(10) Patent No.: US 9,566,335 B1
(45) Date of Patent: Feb. 14, 2017

(54) PROTEIN SEQUENCING METHOD AND REAGENTS

(75) Inventors: Andrew Emili, Milton (CA); Megan McLaughlin, Toronto (CA); Kyrylo Zagorovsky, Ontario (CA); Jonathan Buchanan Olsen, Kitchener (CA); Warren C. W. Chan, Toronto (CA); Sachdev S. Sidhu, Toronto (CA)

(73) Assignee: The Governing Council of the University of Toronto, Toronto, ON (CA)

( * ) Notice: Subject to any disclaimer, the term of this patent is extended or adjusted under 35 U.S.C. 154(b) by 1079 days.

(21) Appl. No.: 12/891,313

(22) Filed: Sep. 27, 2010

Related U.S. Application Data

(60) Provisional application No. 61/245,875, filed on Sep. 25, 2009.

(51) Int. Cl.
 *G01N 31/00* (2006.01)
 *G01N 33/53* (2006.01)
 *A61K 45/06* (2006.01)

(52) U.S. Cl.
 CPC ..................................... *A61K 45/06* (2013.01)

(58) Field of Classification Search
 CPC ... C07K 16/22; C07K 2317/76; C12N 15/113; A61K 2039/505; A61K 45/06; G01N 33/6893
 See application file for complete search history.

(56) References Cited

U.S. PATENT DOCUMENTS

| | | | |
|---|---|---|---|
| 4,548,904 | A | 10/1985 | Kent et al. |
| 5,591,646 | A * | 1/1997 | Hudson et al. .................... 506/9 |
| 6,846,638 | B2 | 1/2005 | Shipwash |
| 2004/0175822 | A1 | 9/2004 | Timperman |
| 2007/0231925 | A1 | 10/2007 | Chhabra et al. |
| 2008/0085840 | A1 | 4/2008 | Buzby |
| 2008/0299565 | A1 | 12/2008 | Schneider et al. |
| 2009/0061447 | A1 | 3/2009 | Schneider |

FOREIGN PATENT DOCUMENTS

WO    WO 2007/120805 A2 * 10/2007  ............. C40B 40/10

OTHER PUBLICATIONS

Erbse et al. (Nature, vol. 439, No. 9, Feb. 2006, pp. 753-756.*
Fonovic et al., Molecular & Cellular Proteomics, 2007, vol. 6, pp. 1761-1770).*
Hafok-Peters et al. Biomedical and Environmental Mass, 1990, vol. 19, pp. 159-163).*
Ray and Norden (FASEB Journal, vol. 14, 2000, pp. 1041-1060).*
Erbse et al. (Nature, vol. 439, No. 9, Feb. 2006, pp. 753-756).*
Guo et al. (The Journal of Biological Chemistry, Vo.277, No. 48, 2002, pp. 46753-46762).*
Wang et al. (Molecular Cell, vol. 32, 2008, pp. 406-414).*
Harris et al. "Single-Molecule DNA Sequencing of a Viral Genome. " Science, Apr. 4 2008: vol. 320. No. 5872.
Tasaki et al. "The substrate recognition domains of the N-end rule pathway." Journal of Biological Chemistry, Jan. 16, 2009: vol. 284, No. 3, pp. 1884-1895.
Schuenemann et al. "Structural basis of N-end rule substrate recognition in *Escherichia coli* by the ClpAP adaptor protein ClpS." EMBO Reports, 2009, vol. 10, No. 5.
Roman-Hernandez et al. Molecular basis of substrate selection by the N-end rule adaptor protein ClpS. PNAS, Jun. 2, 2009; vol. 106, No. 22, pp. 8888-8893.
Chen et al. "Effect of Linker for Immobilization of Glutathoine on BSA-Assembled Controlled Pore Glass Beads." Bull. Kor. Chem. Soc., 2004, vol. 25, No. 9, pp. 1366-1370.
Wang et al. "The Molecular Basis of N-end Rule Recognition." Molecular Cell, Nov. 7, 2008: 32:406-414.

\* cited by examiner

*Primary Examiner* — Lisa Cook
(74) *Attorney, Agent, or Firm* — Bereskin & Parr LLP/S.E.N.C.R.L., s.r.l.; I. Laurence MacPhie

(57) ABSTRACT

The invention describes methods and reagents useful for sequencing polypeptide molecules. The method comprises affixing a polypeptide to a substrate and contacting the polypeptide with a plurality of probes. Each probe selectively binds to an N-terminal amino acid or an N-terminal amino acid derivative. Probes bound to the polypeptide molecule are then identified before cleaving the N-terminal amino acid or N-terminal amino acid derivative of the polypeptide. Also provided are methods for the sequencing a plurality of polypeptide molecules in a sample and probes specific for N-terminal amino acids or N-terminal amino acid derivatives.

17 Claims, 11 Drawing Sheets

FIG. 4

| | | 27 | 31 | 44 | 61 | 69 | SEQ ID NO: |
|---|---|---|---|---|---|---|---|
| A | | | | | | | |
| ClpS_E. coli | | HYKV | ILVNDDYTPM | EFVI | ...... | LMLAVHYQG | 6 (...) 7 |
| ClpS_C. crescentus | | LYRV | LILNDDYTPM | EFVV | ...... | IMLRVHQNG | 8 (...) 9 |
| ClpS_P. aeruginosa | | LYKV | VLFNDDYTPM | DFVV | ...... | IMLTVHTQG | 10 (...) 11 |
| ClpS_M. tuberculosis | | AWVT | IVWDDFVELM | SYVT | ...... | LMLQVHNEG | 12 (...) 13 |
| ClpS_Synechococcus | | RYKV | LLHNDFVHSM | EYVV | ...... | VMLEAHNSG | 14 (...) 15 |
| UBR1_YEAST | | NYTV | IIYNDEYNNY | SQAT | ...... | LTSRIDGER | 16 (...) 17 |
| UBR1_HUMAN | | RYYC | VLFNDEHHSY | DHVI | ...... | HTIAIDKEG | 18 (...) 19 |
| UBR2_HUMAN | | YYYC | MLFNDEVHTY | EQVI | ...... | FATYVDRDG | 20 (...) 21 |

FIG. 5

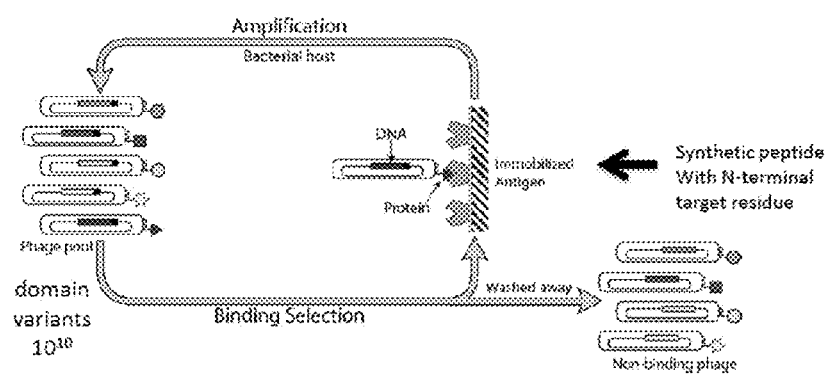

A

B

| | | Peptide or protein immobilized | | | | | | | |
|---|---|---|---|---|---|---|---|---|---|
| | Sequence | RSLDFVE QVQVVG | RAMDFV GFSQLVG | RSGDFLL NSLFFG | LSSAPVSI DDFIG | LMEDNGV SPVWDG | LSDGMFT AGSLIG | anti-Flag | BSA | NA |
| | N terminus | R | R | R | L | L | L | | | |
| Domain displayed | ClpS (C. crescentus) | 0.08 | 0.10 | 0.09 | 0.16 | 0.09 | 0.14 | 3.70 | 0.08 | 0.08 |
| | ClpS (E. coli) | 0.08 | 0.11 | 0.09 | 1.21 | 0.25 | 1.10 | 4.08 | 0.07 | 0.08 |
| | Fab (Her2) | 0.11 | 0.18 | 0.15 | 0.09 | 0.09 | 0.10 | 3.71 | 0.07 | 0.11 |

MKKNIAFLLASMFVFSIATNAYASNGEDYADDDDKGSKPFSNIKVILVNDDYTPNEFVIDVLQKFFSYDVERATQLML

AVHYQGKAICGVFTAEVASTKVAMVNKYARENESPLLCTLEKASESGEGDFDYEKMANANKGANTEEADSNALQSDAK

GKLEEVATDYGRAIDGFIGDVEGLANGSGATGDFAGENSQKAQVGDGDKEPLMSNFEQYLPELPQSVECHPFYEAGX

PYEFGIDCDKINLPEGVFAPLLYVATPHYVFSTPANILRNKEE* (SEQ ID NO: 3)

FIG. 8
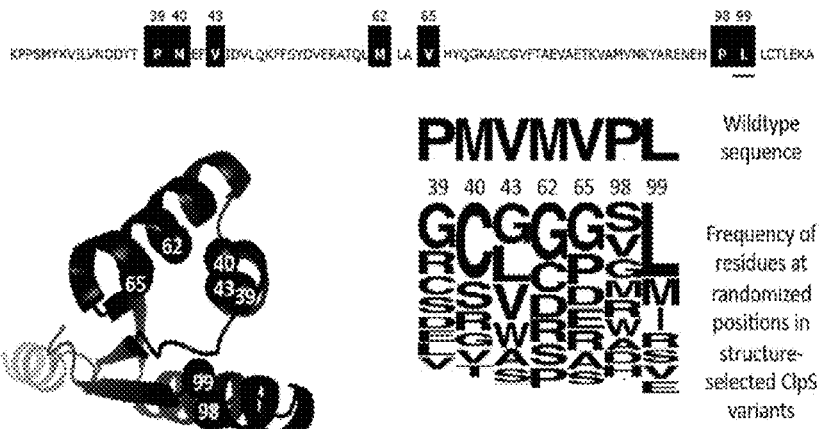
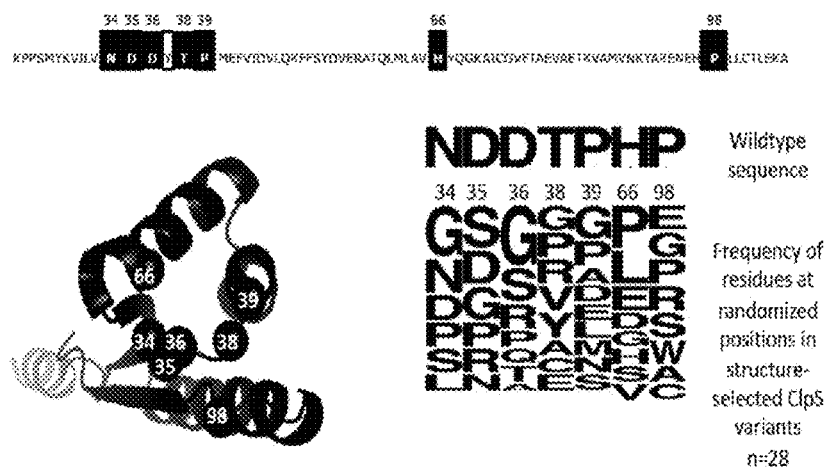

FIG. 9
A
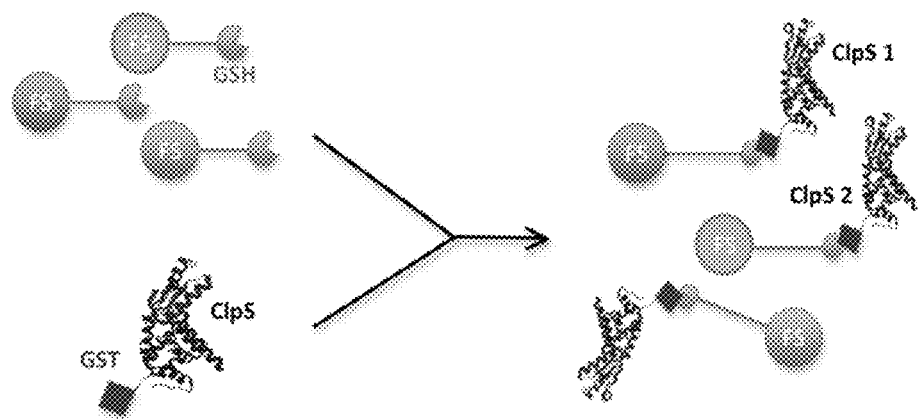
B
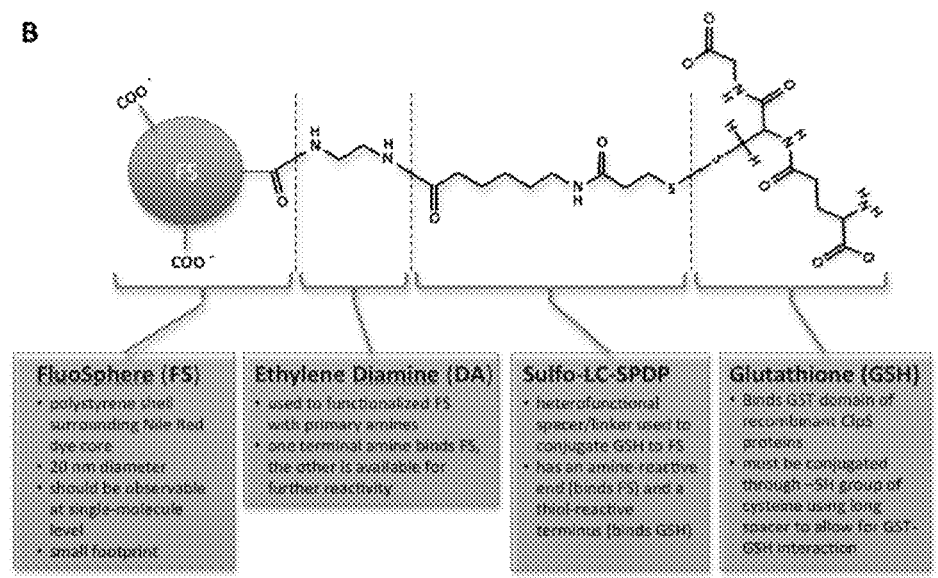

FIG. 11
A
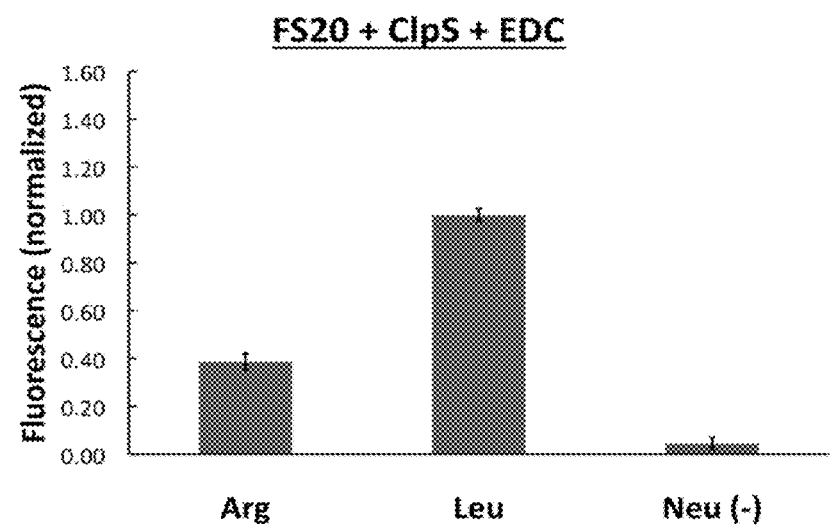
B
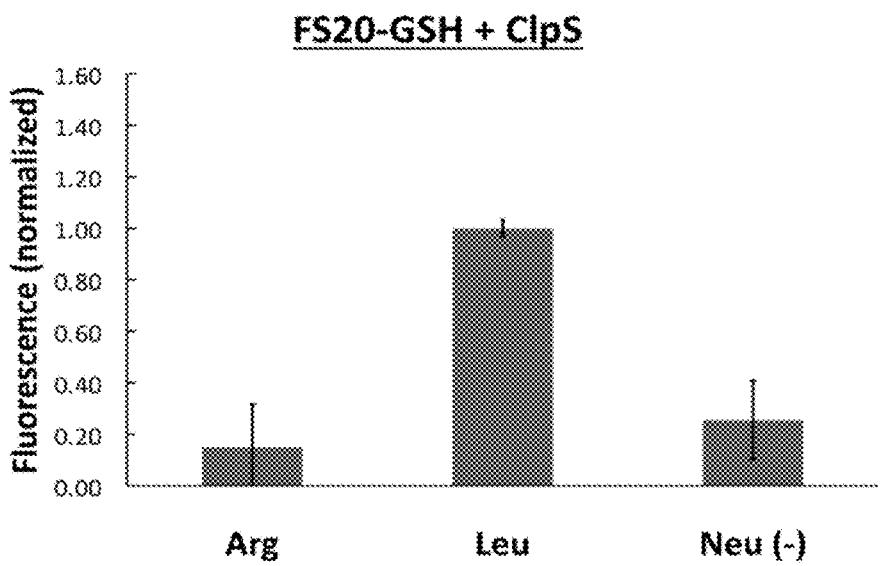

PROTEIN SEQUENCING METHOD AND REAGENTS

CROSS REFERENCE TO RELATED APPLICATIONS

This application claims priority to U.S. provisional application No. 61/245,875 titled SINGLE MOLECULE PROTEIN SEQUENCING METHOD filed on Sep. 25, 2009, the contents which of are herein incorporated by reference.

NON-PUBLICATION REQUEST

A non-publication request has been submitted with this application upon filing. This application is not to be published under 35 U.S.C. 122(b)

INCORPORATION OF SEQUENCE LISTING

A computer readable form of the Sequence Listing "13795-P35487US01_Sequence_Listing.txt" (8,919 bytes), submitted via EFS-WEB and amended on Apr. 2, 2014, is herein incorporated by reference.

FIELD OF THE INVENTION

This invention relates to the field of protein sequencing. More specifically, the invention relates to methods, assays and reagents for sequencing protein or polypeptide molecules as well as to methods and assays for the parallel sequencing of proteins or polypeptides.

BACKGROUND OF THE INVENTION

Proteins mediate the biological activity, and function, of virtually every biological process in cells, while misexpression is associated with various human diseases. The identification and quantification of proteins present in biological samples is therefore a fundamental problem applicable to most biomedical research studies, and a cornerstone of the emerging field of Proteomics.

Protein sequencing has traditionally relied on the sequential detection of individually cleaved N-terminal amino acids from a population of identical polypeptide molecules using Edman degradation chemistry and the detection and identification of the different amino acid Edman derivatives using techniques such as differential HPLC retention and UV absorption. More recently, mass spectrometry has been used to sequence and/or identify proteins or polypeptides with increased speed, accuracy and sensitivity. These methods are generally low-throughput, computationally demanding and require the use of expensive equipment. However, even the most sensitive mass spectrometers require relatively large amounts of sample, with current limits of detection on the order of $10^8$ molecules (equivalent to nanogram or femtomole levels) and are not able to exhaustively sequence complex mixtures of proteins due to ion-ion interference, preferential (biased) detection of certain molecules, limited dynamic range and general under-sampling.

While dramatic improvements have been made in the past couple of years with respect to the speed, comprehensiveness and availability of high-throughput massively parallel DNA sequencing platforms capable of sequencing large numbers of different nucleic acid molecules simultaneously, advances in mass spectrometer performance have been incremental. Relatively little progress has been made towards the development of "next generation" platforms for global protein sequencing at the individual single molecule level. Furthermore, the relative complexity of protein mixtures such as blood, tissue or cell extracts, as well as the lack of PCR-based amplification or properties such as duplex formation and base-pairing, have hampered the development of single-molecule protein sequencing such as those described for polynucleotides (Harris et al. Science 4 Apr. 2008: Vol. 320. no. 5872).

Accordingly, there remains a need for novel methods and assays for sequencing single polypeptide molecules and for methods and assays able to perform the simultaneous parallel sequencing of large-numbers of polypeptides present in one or more samples.

SUMMARY OF THE INVENTION

In a broad aspect there are provided methods for sequencing polypeptides wherein the polypeptides are contacted with probes that selectively bind to N-terminal amino acid residues. In another broad aspect, there are provided probes that selectively bind to N-terminal amino acid residues. In one embodiment the methods and reagents are useful for sequencing a single polypeptide molecule, multiple molecules of a single polypeptide, or for the parallel sequencing of a plurality of different polypeptides. The described methods and reagents are also useful for the massively parallel sequencing of mixtures of proteins, such as for the analysis of single cells or biological or environmental samples. In a further aspect, the methods are useful for the both the qualitative (i.e. determining the sequence identity) and quantitative (i.e. determining the abundance) analysis of protein expression in one or more samples.

Accordingly, in one embodiment, there is provided a method of sequencing a polypeptide comprising affixing the polypeptide to a substrate and contacting the polypeptide with a plurality of probes where each probe selectively binds to an N-terminal amino acid or a N-terminal amino acid derivative. The probe bound to the polypeptide is then detected thereby identifying the N-terminal amino acid of the polypeptide. In one embodiment, the N-terminal amino acid or N-terminal amino acid derivative of the polypeptide is cleaved, and the steps of contacting the polypeptide with a plurality of probes, detecting the probe bound to the polypeptide, and cleaving the N-terminal amino acid of the polypeptide are repeated to determine the sequence of at least a portion of the polypeptide. In some embodiments, rinse or wash steps are included before or after each step of the method. Optionally, the polypeptide is a single polypeptide molecule.

In one embodiment, one or more polypeptides are affixed to a substrate and contacted with a plurality of probes before washing the substrate to remove any non-specifically bound probes.

In one embodiment, the N-terminal amino acid of a polypeptide affixed to the substrate is derivatized prior to contacting the polypeptide with the plurality of probes. For example, in one embodiment the N-terminal amino acid is derivatized with an Edman reagent such as phenyl isothiocyanate (PITC).

In one embodiment, the polypeptide is affixed to the substrate through a C'-terminal carboxyl group or a side chain functional group of the polypeptide. In some embodiments the polypeptide is covalently or non-covalently affixed to the substrate.

In one embodiment, the substrate is optically transparent. For example, the substrate is optionally a glass slide or silicon wafer. Optionally, the substrate is embedded in a microfluidic device.

In one embodiment, the substrate comprises a plurality of spatially resolved attachment points. In some embodiments, the attachment points include a molecular linker, such as a polyethylene glycol (PEG) moiety. In some embodiments, the polypeptide is affixed to the substrate through a spatially resolved attachment point.

In one embodiment, the polypeptide affixed to the substrate is contacted with a plurality of probes. In one embodiment, the plurality of probes includes one or more probes that selectively bind to one of 20 natural proteinogenic amino acids, one or more probes that selectively bind to a post-translationally modified amino acid, or one or more probes that selectively bind to an amino acid derivative or modified amino acid derivative. In one embodiment, the probes selectively bind a N-terminal amino acid or a N-terminal amino acid derivative. The 20 natural proteinogenic amino acids include those amino acids commonly found in proteins and coded for by the standard genetic code. In some embodiments, the amino acid derivative is an Edman reagent derivative such as a phenylthiocarbamyl (PTC) derivative.

In some embodiments, the probe comprises an affinity capture reagent and one or more detectable labels. Optionally, the affinity capture reagent is a synthetic or natural antibody. In some embodiments, the affinity capture reagent is an aptamer. In one embodiment, the affinity capture reagent is a polypeptide, such as a modified member of the ClpS family of adaptor proteins. Optionally, the probe comprises a variant of a E. Coli ClpS binding polypeptide, wherein the variant has at least 80% sequence identity to the polypeptide set forth in SEQ ID NO: 1. In one embodiment, the probe comprises a polypeptide with at least 80% sequence identity to the polypeptide set forth in SEQ ID NO: 2 and is selective for N-terminal tryptophan residues.

In one embodiment, the detectable label is optically detectable. In some embodiments, the detectable label comprises a fluorescently moiety, a color-coded nanoparticle, a quantum dot or any combination thereof. In one embodiment the label comprises a polystyrene dye encompassing a core dye molecule such as a FluoSphere™.

In one embodiment, the probe bound to the polypeptide affixed to the substrate is detected by directly or indirectly detecting the detectable label. In some embodiments, the probe is detected using an optical detection system. Optionally, the optical detection system comprises a CCD camera and/or a rastering laser/scanner. In some embodiments, the optical detection system has single-photon resolution.

In one embodiment of the method described herein, the N-terminal amino acid of the polypeptide affixed to the substrate is cleaved. In one embodiment, the N-terminal amino acid or N-terminal amino acid derivative is cleaved using Edman degradation. For example in one embodiment, the Edman degradation proceeds through the addition of phenylisothiocyanate under alkaline conditions to form a cyclical phenylthiocarbamoyl derivative followed by cleavage of the N-terminal amino acid under acidic conditions. In one embodiment, the N-terminal amino acid is derivatized at a pH of between 8 and 10, and the step of cleaving the N-terminal amino acid occurs at a pH of between 2 and 6.

In one embodiment, the polypeptide to be sequenced is a partially digested or completely digested protein. In a further embodiment, a sample comprising a plurality of polypeptides is treated with an endopeptidase in order to partially or completely digest the polypeptides contained in the sample. In one embodiment, the polypeptide or sample is digested prior to being affixed to the substrate.

In another aspect, there is provided a method of sequencing a plurality of polypeptide molecules in a sample comprising affixing the polypeptide molecules in the sample to a plurality of spatially resolved attachment points on a substrate and contacting the polypeptides with a plurality of probes, wherein the probes selectively bind to an N-terminal amino acid or a N-terminal amino acid derivative. In one embodiment, for each polypeptide molecule that is spatially resolved and affixed to the substrate, the probe bound to each polypeptide is identified. In a further embodiment, the N-terminal amino acid or N-terminal amino acid derivative of each of the polypeptides is cleaved. In one embodiment, the steps of contacting the plurality of peptides with a plurality of probes, identifying the probes bound to the polypeptides and cleaving the N-terminal amino acid of the polypeptide are repeated in order to determine the sequence of at least a portion of each polypeptide molecule that is spatially resolved and affixed to the substrate.

In one embodiment, the N-terminal amino acid residues of the polypeptides affixed to the substrate are derivatized prior to contacting the polypeptide with the plurality of probes. For example the N-terminal amino acid residues may be derivatized with an Edman reagent, such as PITC.

In some embodiments, rinse or wash steps are included before or after each step of the methods described herein.

In some embodiments, the sample comprises a cell extract or tissue extract. In one embodiment, the sample comprises a single cell. In some embodiments, the sample is a biological fluid such as blood, plasma. The sample may also comprise an environmental sample such as a soil sample or other biological material.

In some embodiments, the sequence information generated using the methods described herein is used to search a reference sequence database. For example, in one embodiment, a sequence database is searched using the complete or partial sequence of a polypeptide in order to determine the identity of the polypeptide.

In another embodiment, the methods described herein are useful for the quantitative analysis of polypeptide in a sample. For example, the number of instances of a particular polypeptide in a sample can be determined by comparing the sequence or partial sequence of each polypeptide, grouping similar polypeptide sequences and counting the number of instances of each similar polypeptide sequence.

In one aspect, the description provides probes that selectively bind to an N-terminal amino acid or N-terminal amino acid derivative of a polypeptide. In one embodiment, the probe comprises an antibody or antibody fragment. In another embodiment, the probe comprises an affinity capture binding reagent. In some embodiments, the affinity capture binding reagent is an aptamer. In one embodiment, the probes further comprise a detectable label such as a fluorescent moiety.

In one embodiment, there is provided a probe comprising a variant of a polypeptide wherein the variant binds to an N-terminal amino acid or a N-terminal amino acid derivative with a different selectivity than the polypeptide. In one embodiment, probe comprises a variant ClpS polypeptide, and the variant polypeptide binds to an N-terminal amino acid with a different selectivity than the ClpS polypeptide. Optionally, the ClpS polypeptide is a truncated E. coli ClpS polypeptide comprising the following sequence:

(SEQ ID NO: 1)
KPPSMYKVILVNDDYTPMEFVIDVLQKFFSYDVERATQLMLAVHYQGKAIC

GVFTAEVAETKVAMVNKYARENEHPLLCTLEKA

The inventors have determined that variant ClpS polypeptides with mutations at specific positions in the sequence set forth in SEQ ID NO: 1 are useful for selectively binding specific N-terminal amino acids and for the sequencing methods described herein. In one embodiment, the variant polypeptides show selectivity for N-terminal amino acids compared to the parent polypeptide used to generate the variant, such as wildtype ClpS. In one embodiment, the probes show affinity for different N-terminal amino acids compared to wildtype ClpS. In one embodiment, the probes comprise variant ClpS polypeptides with one or more substitutions, insertion, deletions or additions at residues that correspond to residues 12, 13, 14, 16, 17, 18, 21, 40, 43, 44, 76 and 77 as set forth in SEQ ID NO: 1. In one embodiment, the probes comprise variant ClpS polypeptides with one or more mutations at ligand specificity pocket residues selected from residues that correspond to positions 17, 18, 21, 40, 43, 76 and 77 as set forth in SEQ ID NO: 1. In one embodiment, the probes comprise variant ClpS polypeptides with one or more mutations at alpha amino binding residues selected from residues that correspond to positions 12, 13, 14, 16, 17, 44, and 76 as set forth in SEQ ID NO: 1. In one embodiment, the probe comprises a variant of SEQ ID NO: 1, wherein residue positions 21 and 40 are cystein.

In one embodiment, there is provided a N-terminal amino acid probe selective for tryptophan that comprises the following polypeptide sequence (substitutions relative to SEQ ID NO: 1 shown in underline):

(SEQ ID NO: 2)
KPPSMYKVILVNDDYTP<u>A</u>EF<u>C</u>IDVLQKFFSYDVERATQL<u>CL</u>A<u>A</u>HYQGKAIC

GVFTAEVAETKVAMVNKYARENEH<u>AA</u>LCTLEKA

In one embodiment, the probe comprises a variant ClpS polypeptide with at least 70%, 80%, 90%, or 95% sequence identity to SEQ ID NO: 1 or to SEQ ID NO: 2.

In another aspect, the probes are directly or indirectly labeled with a detectable label. In one embodiment, the probes are indirectly labeled through conjugation of a glutathione transferase (GST) domain and glutathione. In one embodiment, the probes are directly labeled through covalent attachment of the detectable label and the probe. In one embodiment, the detectable label is a fluorescent label such as a FluoSphere™.

The one aspect, there is also provided a cloned DNA sequence encoding a polypeptide that selectively binds an N-terminal amino acid enzyme. In one embodiment, the cloned DNA sequence encodes a polypeptide with the sequence set forth in SEQ ID NO: 1 or SEQ ID NO: 2.

In one aspect, there is provided a method for producing polypeptides that selectively bind N-terminal amino acids. In one embodiment, the method comprises generating a plurality of variant polypeptides, expressing the polypeptides using phage display and selecting for variants that selectively bind to one or more N-terminal amino acids. In one embodiment, the variant polypeptides comprise variant ClpS polypeptides. In one embodiment, the variants are selected under competitive conditions. In one embodiment, the method produces polypeptides that selectively bind a target N-terminal amino acid and the competitive conditions include the presence of peptides with N-terminal amino acids others than the target N-terminal amino acid.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

Further features and advantages of the present invention will become apparent from the following detailed description, taken in combination with the appended drawings, in which:

FIG. 4 shows sequence alignment of selected bacterial ClpS proteins (SEQ ID NOS: 6-15) together with the type 2 binding region (UBR box) from the homologous eukaryotic UBR1 and UBR2 proteins (SEQ ID NOS: 16-21) (from Schuenemann et al. *EMBO Reports, Vol.* 10, No. 5, 2009).

FIG. 5 shows directed evolution of engineered protein domains for use in N-terminal amino acid probes using phage display. Large combinatorial libraries, generated by targeted Kunkel mutagenesis or by chemical gene synthesis, of domain variants (~$10^{10}$ unique individuals) can be displayed as fusions to bacteriophage coat proteins, such that the sequence of the displayed protein on a single phage particle is encoded by the genome packaged within. This physical connection between phenotype and genotype makes it possible to select a displayed variant based on its binding properties, and then to obtain its sequence from the encapsulated phage genome. Selections are performed by immobilizing the ligand of interest to a solid support, allowing the library of variants an opportunity to bind, and then washing away all phage that fail to bind. The phage that do bind the ligand are retained, and infected into bacteria in order to replicate. The same selection procedure can then be repeated with the new subpopulation of phage. After repeated rounds of selection, binders will dominate, at which point individual clones can be isolated, sequenced and subcloned for expression as recombinant proteins and further biochemical characterization.

FIG. 7A: Sidechain specificity is dictated by the shape and chemical composition of the hydrophobic pocket, mediated by sidechains of the highlighted residues. Highlighted residues were chosen for randomization based on analysis of the ClpS structure and available data; their sidechains contribute to the hydrophobic pocket either directly or by influencing the orientation of direct contacts (i.e. two proline residues). FIG. 7B: alpha-amino recognition depends on a network of hydrogen bonds mediated by the residues shown at positions 34, 35, 36, 38 and 66, through a combination of sidechain and main chain interactions. The two proline residues shown at positions 39 and 98 influence the orientation of these critical residues as well.

FIG. 8 shows that ClpS (SEQ ID NO: 22) is structurally tolerant of diverse residues at key specificity mediating positions. Protease-resistant, likely well-folded variants, were selected from each library using an immobilized anti-FLAG antibody. The distribution of residues at each randomized position in each set of structure-selected ClpS variants is shown as a frequency logo. FIG. 8A: Positions in the sidechain specificity pocket are surprisingly structurally tolerant to a wide variety of substitutions. The exclusively hydrophobic residues in the wildtype domain can also be substituted with polar or charged residues. FIG. 8B: Alpha-amino recognition residues are also quite structurally tolerant to substitution. The set of structurally-tolerated residues at each of these positions informs subsequent library design, and provides a useful basis for comparison for residue frequencies observed in function-selected variants.

FIG. 9 shows an indirect labeling methodology for optical detection of recombinant probes. FIG. 9A: FluoSpheres (FS) functionalized with glutathione (GSH) bind the GST domain of the recombinant ClpS proteins. Each population of ClpS protein can be tagged with its own colour label in a simple one-step process that requires no chemical modification. FIG. 9B: Bioconjugation scheme to adsorb GSH onto Fluo-Sphere surface in a manner that does not inhibit GST binding. FS surface, initially containing carboxylic acid, is first reacted with ethylene diamine to provide amine groups on the FluoSphere surface, which are further used to react with Sulfo-LC-SPDP. Reaction with Sulfo-LCSPDP leaves a thiol reactive end, which reacts with GSH upon mixing.

FIG. 11 shows the optical detection of preferential ligand binding by labeled ClpS probes. FIG. 11A: Immobilized peptide binding signal obtained with immobilized peptides probed using ClpS covalently attached to fluospheres using EDC linker. FIG. 11B: Binding signal produced with Fluo-spheres attached to probe using indirect non-covalent GST-GSH interaction. Both labeled probes show a fluorescent signal indicating preferential binding to the target Leucine N-terminal amino acid.

FIG. 12 A: Sequence of the wildtype ClpS domain from *E. coli* that recognizes N-terminal F, L, Y and W residues (SEQ ID NO: 1) (top) and the engineered variant that binds N-terminal W residues selectively (SEQ ID NO: 2) (bottom) with key residues highlighted. FIG. 12B: structure of wildtype ClpS in complex with Lpep (PDB: 2W9R) with diversified residues in the displayed library shown as highlighted. FIG. 12C: Key residues in the novel ClpS variant W1 are indicated on the wildtype structure.

DETAILED DESCRIPTION OF THE INVENTION

Figure 1:
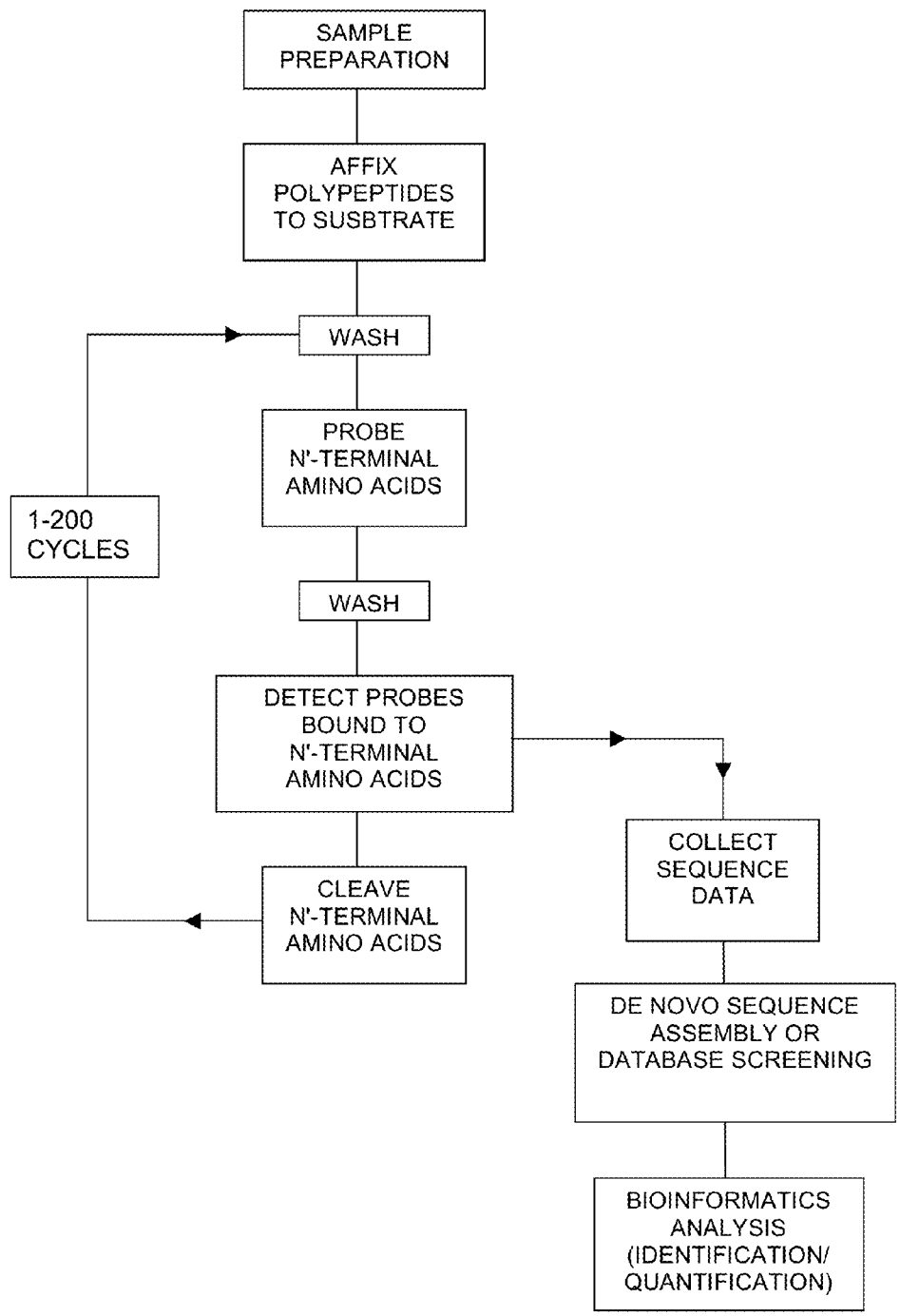
FIG. 1 is a schematic showing one embodiment of a method for sequencing polypeptides as described herein.

The present description provides methods, assays and reagents useful for sequencing proteins. In one aspect, the methods are useful for sequencing single polypeptide molecules or multiple molecules of a single polypeptide. In one aspect, the methods and reagents are useful for determining the N-terminal amino acid of a polypeptide. In one aspect, the methods are useful for the simultaneous sequencing of a plurality of single polypeptide molecules, such as for the basis of massively parallel sequencing techniques. Accordingly samples comprising a mixture of different proteins can be assayed according to the methods described herein to generate sequence information regarding individual protein molecules in the sample. In a further aspect, the methods are useful for protein expression profiling in complex samples. For example, the methods are useful for generating both quantitative (frequency) and qualitative (sequence) data for proteins contained in a sample.

In a further aspect, the description provides reagents such as N-terminal amino acid affinity capture reagents and probes comprising N-terminal amino acid affinity capture reagents suitable for practicing the methods described herein. In one embodiment, probes are variant ClpS polypeptides generated as set forth in Example 4. In one embodiment, the probes comprise readily detectable labels, such as fluorescent dyes.

The inventors have determined that probes specific for an N-terminal amino acid of a polypeptide, or specific for a derivative of a N-terminal amino acid of a polypeptide, can be used to generate sequence information by sequentially identifying and then cleaving the N-terminal amino acids of a polypeptide. The inventors have also determined that by first affixing the polypeptide molecule to a substrate, it is possible to determine the sequence of that immobilized polypeptide by iteratively detecting which probes are bound to the polypeptide at that same location on the substrate. Each probe may contain one or more detectable label(s) that facilitates the identification of specific probes.

Accordingly, in one embodiment there is provided a method of sequencing a polypeptide comprising:
a) affixing the polypeptide to a substrate;
b) contacting the polypeptide with a plurality of probes, wherein each probe selectively binds to an N-terminal amino acid or a N-terminal amino acid derivative;
c) detecting the probe bound to the polypeptide molecule, thereby identifying the N-terminal amino acid of the polypeptide;
d) cleaving the N-terminal amino acid or N-terminal amino acid derivative of the polypeptide; and e) repeating steps (b) to (d) to determine the sequence of at least a portion of the polypeptide.

Optionally, step a) comprises affixing a plurality of polypeptides with the same sequence to the substrate and step c) comprises detecting a plurality of probes. In one embodiment, the polypeptide comprises a single polypeptide molecule and step c) comprises detecting a single probe bound to the polypeptide molecule.

In another embodiment, there is provided a method of sequencing a plurality of polypeptide molecules in a sample comprising:
a) affixing the polypeptide molecules in the sample to a plurality of spatially resolved attachment points on a substrate;
b) contacting the polypeptides with a plurality of probes, wherein each probe selectively binds to an N-terminal amino acid or a N-terminal amino acid derivative;
c) for a plurality of polypeptide molecules that are spatially resolved and affixed to the substrate, detecting the probe bound to each polypeptide;
d) cleaving the N-terminal amino acid or N-terminal amino acid derivative of each of the polypeptides; and
e) repeating steps b) to d) to determine the sequence of at least a portion of one or more of the plurality of polypeptide molecules that are spatially resolved and affixed to the substrate.

As used herein, "polypeptide" refers to two or more amino acids linked together by a peptide bond. The term "polypeptide" includes proteins that have a C-terminal end and an N-terminal end as generally known in the art and may be synthetic in origin or naturally occurring. As used herein "at least a portion of the polypeptide" refers to 2 or more amino acids of the polypeptide. Optionally, a portion of the polypeptide includes at least: 5, 10, 20, 30 or 50 amino acids, either consecutive or with gaps, of the complete amino acid sequence of the polypeptide, or the full amino acid sequence of the polypeptide.

As used herein the phrase "selectively binds to an N-terminal amino acid or a N-terminal amino acid derivative" refers to a probe with a greater affinity for one or more target N-terminal amino acids or for one or more N-terminal amino acid derivatives compared to other N-terminal amino acids or N-terminal amino acid derivatives. A probe selectively binds a target N-terminal amino acid or N-terminal amino acid derivatives if there is a detectable relative increase in the binding of the probe to a target N-terminal amino acid or N-terminal amino acid. For example, as shown in Example 4 and Table 2 the ClpS Variant 1 polypeptide selectively binds tryptophan N-terminal amino acids and the ClpS Variant 2 selectively binds arginine and leucine N-terminal amino acids. Optionally, a probe that is selective is specific for a single N-terminal amino acid or N-terminal amino acid derivative. Optionally, a probe that is selective for a N-terminal amino acid or N-terminal amino acid derivative has at least 25%, 50%, 100%, 200%, or greater than 200% more affinity for a target N-terminal amino acid or N-terminal amino acid derivative compared to a non-target N-terminal amino acid or N-terminal amino acid derivative. In one embodiment, the probes selectively bind the N-terminal amino acid or N-terminal amino acid derivative with an 1050 of 10 micromolar or better.

The phrase "N-terminal amino acid" refers to an amino acid that has a free amine group and is only linked to one other amino acid by a peptide bond in the polypeptide. The phrase "N-terminal amino acid derivative" refers to an N-terminal amino acid residue that has been chemically modified, for example by an Edman reagent or other chemical in vitro or inside a cell via a natural post-translational modification (e.g. phosphorylation) mechanism.

As used herein, "sequencing a polypeptide" refers to determining the amino acid sequence of a polypeptide. The term also refers to determining the sequence of a segment of a polypeptide or determining partial sequence information for a polypeptide.

As used herein, "affixed" refers to a connection between a polypeptide and a substrate such that at least a portion of the polypeptide and the substrate are held in physical proximity. The term "affixed" encompasses both an indirect or direct connection and may be reversible or irreversible, for example the connection is optionally a covalent bond or a non-covalent bond.

As used herein "the cleaving the N-terminal amino acid or N-terminal amino acid derivative of the polypeptide" refers to a chemical reaction whereby the N-terminal amino acid or N-terminal amino acid derivative is removed from the polypeptide while the remainder of the polypeptide remains affixed to the substrate.

As used herein the term "sample" includes any material that contains one or more polypeptides. Samples may be biological samples, such as biopsies, blood, plasma, organs, organelles, cell extracts, secretions, urine or mucous, tissue extracts and other biological samples of fluids both natural or synthetic in origin. The term sample also includes single cells. The sample may be derived from a cell, tissue, organism or individual that has been exposed to an analyte (such as a drug), or subject to an environmental condition, genetic perturbation, or combination thereof. The organisms or individuals may include, but are not limited to, mammals such as humans or small animals (rats and mice for example).

As used herein, the term "spatially resolved" refers to an arrangement of two or more polypeptides on a substrate wherein chemical or physical events occurring at one polypeptide can be distinguished from those occurring at the second polypeptide. For example, two polypeptides affixed on a substrate are spatially resolved if a signal from a detectable label bound to one of the polypeptides can be unambiguously assigned to one of the polypeptides at a specific location on the substrate.

Substrate Materials

In one embodiment, polypeptides to be sequenced are affixed to a substrate. In some embodiments, the substrate is made of a material such as glass, quartz, silica, plastics, metals, composites, or combinations thereof. In one embodiment, the substrate is a flat planar surface. In another embodiment, the substrate is 3-dimensional and exhibits surface features. In some embodiments, the substrate is a chemically derivatized glass slide or silica wafer.

In one embodiment, the substrate is made from material that does not substantially affect the sequencing reagents and assays described herein. In one embodiment, the substrate is resistant to the basic and acidic pH, chemicals and buffers used for Edman degradation. The substrate may also be covered with a coating. In some embodiments, the coating is resistant to the chemical reactions and conditions used in Edman degradation. In some embodiments, the coating provides attachment points for affixing polypeptides to the substrate, and/or repelling non-specific probe adsorption.

In some embodiments, the surface of the substrate is resistant to the non-specific adhering of polypeptides or debris, so as to minimize background signals when detecting the probes.

In one embodiment, the substrate made of a material that is optically transparent. As used herein, "optically transparent" refers to a material that allows light to pass through the material. In one embodiment, the substrate is minimally- or non-autofluorescent.

Optionally, the substrate is embedded in a microfluidic device. In one embodiment, the microfluidic device is able to direct the reagents described herein to the surface of the substrate. In another embodiment, multiple substrates are embedded in a microfluidic device.

Affixing Polypeptides to the Substrate

In one embodiment, the polypeptides are affixed to the substrate. Preferably, the polypeptides are affixed to the substrate such that the N-terminal end of the polypeptide is free to allow the binding of N-terminal amino acid probes. Accordingly, in some embodiments the polypeptide is affixed to the substrate through the C-terminal end of the polypeptide, the C-terminal carboxylic acid group or a side chain function group of the polypeptide. In some embodiments, the substrate contains one or more attachment points that permit a polypeptide to be affixed to the substrate.

In some embodiments, the polypeptide is affixed through a covalent bond to the substrate. For example, the surface of the substrate may contain a polyethylene glycol (PEG) or carbohydrate-based coating and the polypeptides are affixed to the substrate via an N-hydroxysuccinimide (NHS) ester PEG linker.

Figure 3:
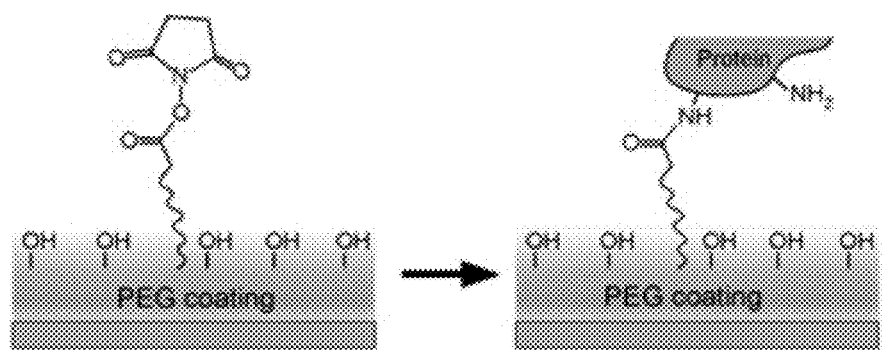
FIG. 3 illustrates one embodiment of affixing a polypeptide to a substrate using a polyethylene glycol (PEG) chemical linker.

FIG. 3 shows one example of a polypeptide linked to a substrate through a PEG-based molecular linker tethered to the surface. A number of different chemistries for attaching linkers and polypeptides to a substrate are known in the art, for example by the use of specialized coatings that include aldehydesilane, epoxysilane or other controlled reactive moieties. In one embodiment, the substrate is glass coated with Silane or related reagent and the polypeptide is affixed to the substrate through a Schiff's base linkage through an exposed lysine residue.

In some embodiments the polypeptide is affixed non-covalently to the substrate. For example, in one embodiment the C-terminal end of the polypeptide is conjugated with biotin and the substrate comprises avidin or related molecules. As shown in Example 4, peptides may be biotinylated and readily attached to a neutravidin substrate and subsequently contacted with N-terminal amino acid probes that bind to the peptides. In another embodiment, the C-terminal end of a polypeptide is conjugated to an antigen that binds to an antibody or related affinity capture reagent on the surface of the substrate. Additional coupling agents suitable for affixing a polypeptide to a substrate have been described in the art (See for example, Athena L. Guo and X. Y. Zhu. *The Critical Role of Surface Chemistry In Protein Microarrays* in Functional Protein Microarrays in Drug Discovery)

Pre-Treatment of the Polypeptide

In one embodiment, the polypeptide or a sample containing one or more polypeptides is pre-treated prior to being affixed on the substrate. For example, the sample may be concentrated and purified to remove contaminating materials, such as by HPLC or nuclease treatment. In another embodiment, the sample may be treated with a protease or peptidase, which cleaves the polypeptide at a specific residue. In one embodiment, the polypeptides are tryptic peptides that are coupled via C-terminal lysine (or arginine) residues, such that the last residue of the polypeptide sequenced is inferred to be K (lysine) or R (arginine).

Washing the Substrate

Optionally, after the polypeptides are affixed to the substrate, the substrate is washed in order to remove any debris such as unbound probe, nucleic acids or other molecules that are not affixed to the substrate that contribute to generating signal noise that interference with the sequencing of specific polypeptide molecules.

In another embodiment, the substrate is treated in order to chemically block any unused attachment points on the surface of the substrate that could result in non-specific binding of probes to the substrate.

N-Terminal Amino Acid Probes

In one aspect of the description, there are provided probes that selectively bind to an N-terminal amino acid or a N-terminal amino acid derivative. In one embodiment, probes that selectively bind to an N-terminal amino acid or an N-terminal amino acid derivative are used to sequence a polypeptide. In some embodiments, the probes are detectable with single molecule sensitivity.

In some embodiments, a probe selectively binds more than one pre-determined N-terminal amino acid. Probes that selectively bind more than one N-terminal amino acid may also be used to determine partial sequence information for a polypeptide.

In one embodiment, the probes include 20 probes that each selectively bind to one of the 20 natural proteinogenic amino acids. In another embodiment, the probes include 20 probes that each selectively bind to a derivative of one of the 20 natural proteinogenic amino acids. In one embodiment, the derivatives are phenylthiocarbamyl derivatives. In a further embodiment, the probes include probes that selectively bind to post-translationally-modified amino acids or their derivatives.

Probes and Affinity Capture Reagents

In one embodiment, the probes comprise an affinity capture reagent. Affinity capture reagents useful for the methods described herein bind to N-terminal amino acids or their derivatives.

In one embodiment, the affinity capture reagent is a natural or synthetic antibody or antibody fragment, or derivative thereof. For example, antibodies that bind to specific amino acid are known in the art and are available commercially from Millipore Corporation (Billerica, Mass.).

In one embodiment, affinity capture reagents and/or analogous N-terminal binding proteins are engineered using phage display (i.e. experimentally via empirical selection) or through rational protein design (i.e. computationally using structural biology concepts/programs, like docking predictions to optimize protein/amino acid ligand interface residues to confer N-terminal residue binding specificity and/or adapt the binding to Edman or other forms of modified N-terminal amino acid residues.

In one embodiment, the probe comprises a variant of a polypeptide wherein the variant binds to an N-terminal amino acid or a N-terminal amino acid derivative with a different selectivity than the polypeptide. As used herein the term "variant" refers to a polypeptide that has one or more substitutions, additions or deletions compared to a reference non-variant polypeptide sequence such as a naturally occurring polypeptide. For example, SEQ ID NO: 2 is a variant of the *E. Coli* ClpS polypeptide as set forth in SEQ ID NO: 1. As used herein, a variant polypeptide has a "different selectivity" than a polypeptide if has a greater affinity for one or more N-terminal amino acids or N-terminal amino acid derivatives than the non-variant polypeptide, or if it exhibits an binding affinity for one or more N-terminal amino acids or a N-terminal amino acid derivatives not seen in the non-variant polypeptide.

In one embodiment, the affinity capture reagent comprises a member of the UBR box recognition sequence family, or a variant of the UBR box recognition sequence family. UBR recognition boxes are described in Tasaki et al. (Journal of Biological Chemistry, Vol. 284, No. 3 pp. 1884-1895 Jan. 16, 2009). Sequence identity between bacterial ClpS proteins and UBR1 and UBR2 is show in FIG. 4.

In a further embodiment, the affinity capture reagent is a member of the evolutionarily conserved ClpS family of adaptor proteins involved in natural N-terminal protein recognition and binding or a variant thereof. The ClpS family of adaptor proteins in bacteria are described in Schuenemann et al. (*Structural basis of N-end rule substrate recognition in Escherichia coli by the ClpAP adaptor protein ClpS*. EMBO reports Vol. 10, No. 5, 2009), and, Roman-Hernandez et al. (*Molecular basis of substrate selection by the N-end rule adaptor protein ClpS*. PNAS Jun. 2, 2009 vol. 106 no. 22 p. 8888-8893). In some embodiments, the amino acid residues corresponding to the ClpS hydrophobic binding pocket identified in Schuenemann et al. are modified in order to generate affinity capture reagents with the desired selectivity. In one embodiment, the ClpS sequences shown in FIG. 4 are modified such as Met40 or Met62 are modified to generate novel affinity capture reagents.

As shown in Examples 1 and 4, ClpS adaptor proteins may be modified in order to selectively bind specific N-terminal amino acids or N-terminal amino acid derivatives. For example, selective N-terminal amino acid probes may be generated by creating variants of the E. Coli ClpS polypeptide as set forth in SEQ ID NO: 1, or of the variant Trp-binding polypeptide as set forth in SEQ ID NO: 2. Other ClpS polypeptides, such as those isolated from different species, may also be modified as described herein to generate N-terminal amino acid binding peptides.

In one embodiment, the variant ClpS polypeptides comprises one or more substitutions, deletions or additions at positions that correspond to residues 12, 13, 14, 16, 17, 18, 21, 40, 43, 44, 76 and 77 as set forth in SEQ ID NO: 1. In one embodiment, the N-terminal amino acid probe comprises a variant ClpS polypeptide with cystein residues at positions 21 and 40 as set forth in SEQ ID NO: 1. Variant ClpS polypeptides with cystein residues at positions that correspond to residues 21 and 40 as set forth in SEQ ID NO: 1 are believed to form a disulfide bridge, thereby increasing the stability of the variant polypeptide.

As used herein a residue position in one sequence "corresponds to" a residue position in another polypeptide sequence if it exists in an equivalent position in the polypeptide sequence, as indicated by primary sequence homology, tertiary structural homology (as shown by, e.g., crystal structure or computer modeling) or functional equivalence. In one embodiment, sequence alignment between two or more ClpS sequences is used to determine sequence corresponding residues. For example, ClpS polypeptide sequences isolated from different species can be aligned to identify residues that correspond to the same position as shown in FIG. 4.

As shown in Example 4 and Table 2, ClpS Variant 1 (SEQ ID NO: 2) gave a strong signal and selectively binds polypeptides with the N-terminal amino acid tryptophan. In one embodiment the probes comprise variants of the polypeptide sequence set forth in SEQ ID NO: 2. In one embodiment, the variants comprise mutations of the amino acid residues that form the specificity binding pocket or alpha-amino binding residues of the ClpS protein.

In one embodiment, the probes comprise polypeptides with at least 70%, 80%, 90% or 95% sequence identity to SEQ ID 1 or SEQ ID NO: 2. As used herein, "sequence identity" refers to the similarity of two polypeptide sequences that are aligned so that the highest order match is obtained. Sequence Identity is calculated according to methods known in the art. For example, polypeptide sequence identity may be calculated using computer programs to determine identity between two sequences. Representative computer programs include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The Smith Waterman algorithm may also be used to determine percentage sequence identity.

Exemplary parameters for determining polypeptide sequence identity include the following: 1) algorithm from Needleman and Wunsch (J. Mol. Biol., 48:443-453 (1970)); 2) BLOSSUM62 comparison matrix from Hentikoff and Hentikoff (Proc. Natl. Acad. Sci. U.S.A., 89:10915-10919 (1992)) 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % sequence identity= (the number of identical residues)/(alignment length in amino acid residues)*100. For this calculation, alignment length includes internal gaps but does not include terminal gaps.

Additional examples of suitable affinity capture reagents include ClpS family related members present in non-bacterial species, including human, or synthetic constructs developed using principled computational modeling procedures or selected through combinatorial genetic mutagenesis methods.

In another embodiment, affinity capture reagents suitable for use in the probes described herein are based on structured RNA molecules. In one embodiment, the affinity capture reagents are aptamers derived by generating/screening randomized nucleic acid libraries.

In one aspect, the probes and affinity capture reagents exhibit high target selectivity and bind to a limited number N-terminal amino acids of their derivatives, or preferably only a single N-terminal amino acid or its derivative. In another aspect, the affinity capture reagents are specific and exhibit a big differential in target to non-target binding/affinity. Additional properties of preferred affinity capture reagents include fast "on" (association) kinetic binding rates, slow "off" (dissociation) rates, and limited non-specific absorption. In one embodiment, the probes and affinity capture reagents exhibit good stability in solution at different buffers/pHs (e.g. stay folded), a long-shelf life, do not require freezing. In one embodiment, the probes and/or affinity capture reagents and can be dried and resolubilized without a significant loss in activity. In one embodiment, the affinity capture reagents are included in a kit for practicing the methods described herein. In another embodiment, the affinity capture reagents are readily synthesized and exhibit a good yield in recombinant or synthetic form. In another embodiment, the affinity capture reagents exhibit good tractability in terms of genetic selection and screening procedures (e.g. subjected to mutagenesis, protein engineering, or phage display, followed by in vitro binding assay robustness and reproducibility.

Detectable Labels

In another aspect of the description, the probes include detectable labels. Detectable labels suitable for use with the present invention include, but are not limited to, labels that can be detected as a single molecule.

In one embodiment, the probes are detected by contacting the probe with a probe-specific antibody and the probe-specific antibody is then detected.

In some embodiments, the probes or labels are detected using magnetic or electrical impulses or signals.

In one embodiment, the labels are optically detectable, such as labels comprising a fluorescent moiety. Examples of optically detectable labels include, but are not limited to fluorescent dyes including polystyrene shells encompassing core dyes such as FluoSpheres™, Nile Red, fluorescein, rhodamine, derivatized rhodamine dyes, such as TAMRA, phosphor, polymethadine dye, fluorescent phosphoramidite, TEXAS RED, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing. Additional detectable labels include color-coded nanoparticles, or quantum dots or FluoSpheres™. In one embodiment, the detectable label is resistant to photobleaching while producing lots of signal (such as photons) at a unique and easily detectable wavelength, with high signal-to-noise ratio.

One or more detectable labels can be conjugated to the affinity capture reagents described herein using techniques known to a person of skill in the art. In one embodiment, a specific detectable label (or combination of labels) is conjugated to a corresponding affinity capture reagent thereby allowing the identification of the affinity capture reagent by means of detecting the label(s).

Figure 10:
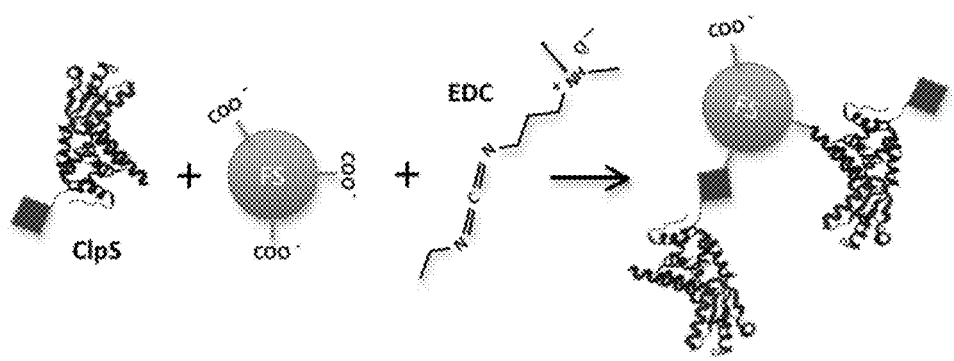
FIG. 10 shows a direct chemical labeling methodology for optical detection of recombinant probes by tagging ClpS proteins or other affinity capture reagents comprising polypeptides with fluorescent labels using an EDC linker. Amines of ClpS proteins are covalently conjugated to carboxylic acids on FluoSpheres through EDC-catalyzed reaction. This labeling approach does not require GSH functionalization of FluoSpheres, but the location of the reacting amine cannot be controlled.

For example, one or more detectable labels can be conjugated to the affinity capture reagents described herein either directly or indirectly as shown in Example 5 and FIGS. 9 and 10.

Detecting Probes Bound to the Polypeptides

In still another aspect of the invention, probes bound to a polypeptide affixed to the substrate are detected, thereby identifying the N-terminal amino acid of the polypeptide. As shown in Example 5, probes comprising a ClpS polypeptide domain can be fluorescently labeled and used to discriminate between N-terminal amino acid residues and generate sequence information.

In one embodiment, the probe is identified by detecting a detectable label (or combination of labels) conjugated to the probe. Methods suitable for detecting the probes described herein therefore depend on the nature of the detectable label(s) used in the method.

In one embodiment, the probes or labels bound to a polypeptide affixed to a substrate are repeatedly detected at that location using a high resolution rastering laser/scanner across a pre-determined grid, unique position or path on a substrate. These methods are useful for the accurate and repeated detection of signals at the same spatially resolved coordinates during each sequencing cycle of the methods described herein. In some embodiments, the polypeptides are randomly affixed to the substrate and the detection of probes proceeds by repeatedly scanning the substrate to identify the co-ordinates and identities of probes bound to polypeptides affixed to the substrate.

In one embodiment, the detecting the probes includes ultrasensitive detection systems that are able to repeatedly detect signals from precisely the same co-ordinates on a substrate, thereby assigning the detected sequence information to a unique polypeptide molecule affixed at that co-ordinate.

In one embodiment, the probes are detected using an optical detection system. Optical detection systems include a charge-coupled device (CCD), near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, total internal reflection fluorescence (TIRF) microscopy, super-resolution fluorescence microscopy, and single-molecule localization microscopy. In general, methods involve detection of laser-activated fluorescence using a microscope equipped with a camera, sometimes referred to as high-efficiency photon detection system. Suitable photon detection systems include, but are not limited to, photodiodes and intensified CCD cameras.

In one embodiment, examples of techniques suitable for single molecule detection of fluorescent probes include confocal laser (scanning) microscopy, wide-field microscopy, near-field microscopy, fluorescence lifetime imaging microscopy, fluorescence correlation spectroscopy, fluorescence intensity distribution analysis, measuring brightness changes induced by quenching/dequenching of fluorescence, or fluorescence energy transfer.

Cleaving the N-Terminal Amino Acid

In a further aspect of the description, the N-terminal amino acid of the polypeptide is cleaved. Cleaving exposes the N-terminus of an adjacent amino acid on the polypeptide, whereby the adjacent amino acid is available for reaction with a probe selective for that amino acid. Optionally, the polypeptide is sequentially cleaved until the last amino acid in the polypeptide (C-terminal amino acid). In some embodiments, the C-terminal amino acid is covalently affixed to the substrate and is not cleaved from the substrate.

Figure 2:
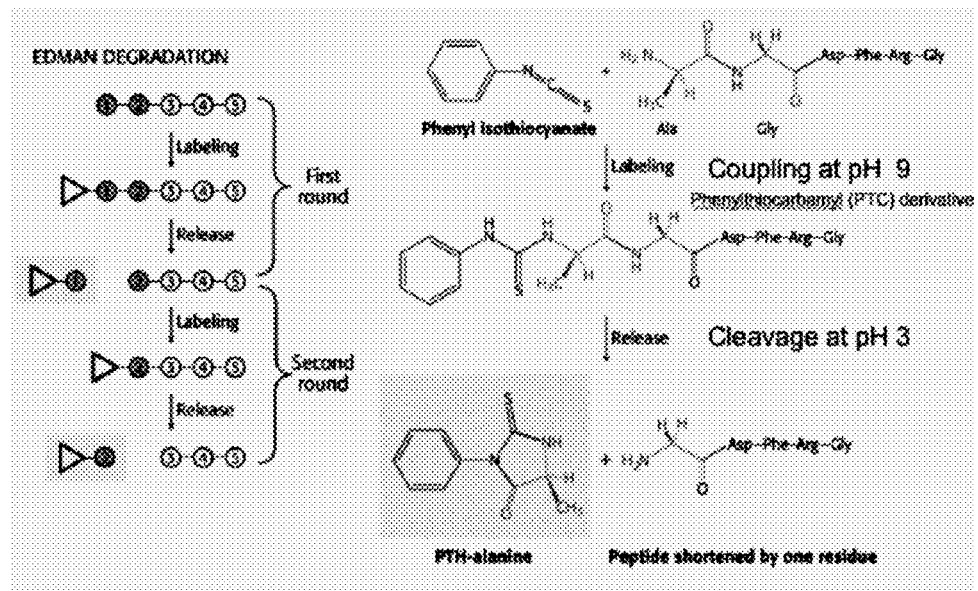
FIG. 2 illustrates one embodiment of N-terminal Edman degradation of a single polypeptide.

In one embodiment, sequential Edman degradation is used to cleave the N-terminal amino acid of the polypeptide. Edman degradation generally comprises two steps, a coupling step and a cleaving step. These steps may be iteratively repeated, each time removing the exposed N-terminal amino acid residue of a polypeptide. As shown in FIG. 2, in one embodiment Edman degradation proceeds by way of contacting the polypeptide with a suitable Edman reagent such as PITC or a PITC analogue at an elevated pH to form a N-terminal phenylthiocarbamyl derivative. Reducing the pH, such by the addition of trifluoroacetic acid results in the cleaving the N-terminal amino acid phenylthiocarbamyl derivative from the polypeptide to form a free anilinothiozolinone (ATZ) derivative. Optionally, this ATZ derivative may be detected, or in another embodiment it may then be washed away from the substrate. In one embodiment the pH of the substrate's environment in controlled in order to control the reactions governing the coupling and cleaving steps.

In some embodiments, the N-terminal amino acid is contacted with a suitable Edman reagent such as PITC or a PITC analogue at an elevated pH prior to contacting the affixed polypeptide with a plurality of probes that selectively bind the N-terminal amino acid derivative. Optionally, the cleaving step comprises reducing the pH in order to cleave the N-terminal amino acid derivative.

In some embodiments, a probe bound to the N-terminal amino acid or its derivative of a polypeptide is removed prior to cleaving the residue.

In one embodiment, the steps of contacting the polypeptide with a plurality of probes, detecting the probe bound to the polypeptide and cleaving the N-terminal amino acid or N-terminal amino acid derivative are repeated in order to sequence the polypeptide. Optionally, the steps are repeated at least 2, 5, 10, 20, 30, 50, or greater than 50 times in order to sequence part of or the complete polypeptide. Optionally at least: 5, 10, 20 30 or 50 contiguous or discontiguous amino acid residues of the amino acid sequence of the polypeptide or the full amino acid sequence of the polypeptide are determined.

In one embodiment, the method includes washing or rinsing the substrate before or after any one of the steps of affixing the substrate, contacting the polypeptide with a plurality of probes, detecting the probe bound to the polypeptide and cleaving the N-terminal amino acid or N-terminal amino acid derivative. Washing or rinsing the substrate removes waste products such as cleaved N-terminal amino acids, debris or previously unused reagents from the substrate that could interfere with the next step in the sequencing assay.

Parallel Sequencing

The methods described herein allow for the sequencing of very large number of polypeptide molecules on a single substrate or on a series of substrates. Accordingly, one aspect of the invention provides for simultaneously sequencing a plurality of affixed polypeptide molecules initially present in a sample. In one embodiment, the sample comprises a cell extract or tissue extract. In some embodiments, the methods described herein may be used to analyze the polypeptides contained in a single cell. In a further embodiment, the sample may comprise a biological fluid such as blood, urine or mucous. Soil, water or other environmental samples bearing mixed organism communities are also suitable for analysis.

In one embodiment of the description, the method includes comparing the sequence of each polypeptide molecule to a reference protein sequence database. In some embodiments, small fragments comprising 10-20 or fewer sequenced amino acid residues may be useful for detecting the identity of a polypeptide in a sample.

In one embodiment, the method includes de novo sequencing of polypeptides in order to generate sequence information about the polypeptide. In another embodiment, the method includes determining a partial sequence or an amino acid pattern and then matching the partial sequence or amino acid patterns with reference sequences or patterns contained in a sequence database.

In one embodiment, the method includes using the sequence data generated by the method as a molecular fingerprint or in other bioinformatic procedures to identify characteristics of the sample, such as tissue type or organismal identity.

In addition, as each polypeptide affixed to the substrate is optionally monitored individually, the method is useful for the quantitative analysis of protein expression. For example, in some embodiments, the method comprises comparing the sequences of each polypeptide, grouping similar polypeptide sequences and counting the number of instances of each similar polypeptide sequence. The methods described herein are therefore useful for molecular counting or for quantifying the number of polypeptides in a sample or specific kinds of polypeptides in a sample.

In a further embodiment, cross-linked polypeptides or proteins are sequenced using the methods described herein. For example, a cross-linked protein may be affixed to a substrate and two or more N-terminal amino acids are then probed and sequenced. The overlapping signals that are detected correspond to probes each binding the two or more N-terminal amino acids at that location. In one embodiment, it is possible to deduce or deconvolute the two multiplexed/mixed sequences via a computational algorithm and DB search.

In a further embodiment, the methods described herein are useful for the analysis and sequencing of phosphopeptides. For example, polypeptides in a sample comprising phosphopeptides are affixed to the surface of the substrate via metal-chelate chemistry. The phosphopolypeptides are then sequenced according to the methods described herein, thereby providing sequence and quantitative information on the phosphoproteome.

The following examples illustrate embodiments of the invention and are not intended to limit the scope of the invention.

Example 1

Affinity Capture Reagents Based on the ClpS Adaptor Protein Scaffold

Phage display and combinatorial site-directed mutagenesis is used to identify variants of the natural N-terminal amino acid binding pocket or structural domain of the ClpS adaptor protein family that selectively bind N-terminal amino acids. Structural modeling of the binding pocket and protein engineering are used to further define modified variants of ClpS family members that are suitable for use with the methods described herein.

Results

Modified ClpS adaptor proteins are selected using screening procedures familiar to those trained in the art. Affinity capture reagents are subsequently identified that exhibit high affinity/selectivity by phage display to N-terminal amino acids.

Example 2

Single Molecule Sequencing of a Synthetic Polypeptide

An artificial test polypeptide comprising of the heptapeptide amino acid sequence TyrPheArgTyrPheArgLys (SEQ ID NO:5) is synthesized. The polypeptide is affixed to a substrate via its C-terminal amino acid carboxy group or the lysine side chain. The substrate is then washed in order to remove any debris. Probes containing an N-terminal affinity capture reagent identified as shown in Example 1 are coupled to a fluorescent moiety. The probes are then added to the substrate under conditions that encourage the binding of the probes to polypeptide. The substrate is then washed to remove any non-specifically bound probes. The probe bound to a single affixed polypeptide is then detected using an optical detection system. The identity of the probe bound to the polypeptide is recorded and the N-terminal amino acid of the polypeptide is cleaved via Edman degradation. Additional rounds of probes are then added to the substrate in order to detect and record the next N-terminal amino acid in the polypeptide prior to cleaving the N-terminal amino acid.

Results

The sequential detection of the probes during each round of sequencing corresponds to the sequence of the artificial polypeptide from the Nterminus to the C-terminus TyrPheArgTyrPheArgLys (SEQ ID NO:5).

Example 3

Validation of Assay Conditions and Protocols

Variants of ClpS are derived via structural modeling, docking, combinatorial site-directed mutagenesis, and/or the experimental selection of high affinity and high specificity binders by phage display as shown in Example 1.

Recombinant ClpS protein is prepared for use as a probe by expression in *E. coli*, or other expression system, and purified using standard biochemical methods, and subsequently coupled with one or more quantum dots with defined absorbance and emission wavelengths, including near infrared fluorescence emitters. The labels can be coupled to an N-terminal region of ClpS that is distinct from the C-terminal domain that serves as the actual peptide ligand (i.e. N-terminal amino acid) binding pocket.

A glass or polystyrene substrate is coated with PEG/NHS, or equivalent reactive carbohydrate linker, to minimize non-specific adsorption and spurious background signal.

The test proteins and peptides include a panel of synthetic peptides of known sequence, some with confirmed binding to ClpS and others with permuted N-terminal residues that aren't recognized by natural forms of ClpS, as reported in the literature, as well as common standard proteins like bovine serum albumin (BSA) and proteolytic digests thereof. A series of test sample dilutions using known amounts and numbers of molecules of the peptides/proteins at specific (serial fold) concentrations are generated prior to peptide coupling.

The test proteins/peptides are then affixed to the substrate, which is washed, and repeatedly probed to assess target detection specificity and affinity, detection limits, non-specific background signal (e.g. probe adsorption) and the response linearity based on molecular counting as a quantitative readout. Quantum dot signals are recorded with a suitable (i.e. CCD-enabled) optical microscope, and specific probe binding signals deconvoluted using suitable filters and software.

Results

The results show single-molecule detection of the test polypeptide sequences. The system exhibits low background and is able to consistently and accurately sequence the test polypeptides.

Example 4

In Vitro Screens Using Phage Display to Identify N-Terminal Amino Acid Probes The present inventors have engineered protein domains that recognize N-terminal residues of polypeptides and are able to discriminate between different residues. Such protein domains are useful for the polypeptide sequencing methods as described herein and also constitute a valuable resource for other applications. The bacterial protein ClpS contains a domain that preferentially binds leucine, phenylalanine, tyrosine and tryptophan N-termini with single-digit micromolar to nanomolar affinities, whereupon it mediates the transfer of these substrates to the ClpAP protease for degradation (Schuenemann et al. (2009) *Structural basis of N-end rule substrate recognition in Escherichia coli by the ClpAP adaptor protein ClpS*. EMBO Reports 10:508-514 2009; Tasaki et al., (2009) *The substrate recognition domains of the N-end rule pathway*. J Biol Chem 284: 1884-1895 2009).

The ClpS binding domain coordinates the alpha-amino group with a network of hydrogen bonds while the side chain specificity in ClpS results from insertion of the first side chain into a hydrophobic pocket.

In order to investigate and identify N-terminal amino acid probes based on the ClpS protein, a truncated wildtype ClpS polypeptide comprising 84 amino acids of wildtype *E. coli* ClpS (See UNIPROT Accession No. POA8Q6) was used as follows:

```
                                          (SEQ ID NO: 1)
1           11          21          31
KPPSMYKVIL  VNDDYTPMEF  VIDVLQKFFS  YDVERATQLM 41          51          61          71          81
LAVHYQGKAI  CGVFTAEVAE  TKVAMVNKYA  RENEHPLLCT  LEKA
```

However, the natural ClpS binding domain has only a limited repertoire of specificities, with only low to moderate selectivity. Using modeling and directed evolution approaches, new domains or "variants" starting with the natural ClpS domain as a scaffold have been generated with different specificities and improved selectivity.

Large custom combinatorial libraries of variants surface displayed on bacteriophage (i.e. phage display) were generated on the basis of available structural information generated by x-ray crystallographic analysis of the ligand binding interfaces. In vitro selection ('panning') was then used to recover subsets of variants with desirable binding properties as shown in FIG. 5. The in vitro selection conditions were manipulated to control the selective pressure for the recovery of highly discriminating binders.

N-terminal affinity capture probes were thereby generated that exhibit (i) highly selective peptide binding (i.e. single N-terminal residue specificities), and (ii) have novel binding capabilities not seen with the wildtype ClpS scaffold).

Phage Display

Figure 6:
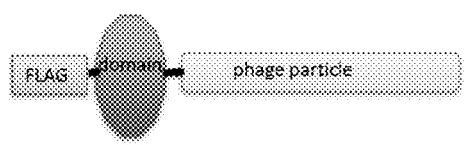
FIG. 6A shows the ClpS domain displayed on page with an N-terminal FLAG tag.
FIG. 6B shows the results of phage binding to immobilized peptides or control peptides assessed using an enzyme linked immunosorbent assay (ELISA). Selected peptide ligands during were synthesized with C-terminal biotin-lysine residues. The biotinylated peptides were immobilized on neutravidin-coated wells of a microtiter plate by passive adsorption, alongside additional control proteins. ClpS from *E. coli* binds two of the Leu-peptides specifically, without cross reactivity to any of the negative controls (bovine serum albumin, BSA; streptavidin, SA; neutravidin, NA). The phage-displayed Fabs are also FLAG-tagged and serve as negative controls for non-specific binding to the immobilized peptides.
FIG. 6C shows the recombinant phage coat protein comprising the ST2 secretion signal, the flag tab, the truncated wild type ClpS polypeptide and gene 3 (SEQ ID NO: 3) used in the phage display experiments as set out in Example 4.

ClpS domains from two different bacterial species (the gram negatives *E. coli* and *Caulobacter crescentus*) were tested to demonstrate that the ClpS domains displayed on phage as N-terminal fusions to a phage surface protein were functional, i.e. able to bind their cognate ligands. The ClpS domains were N-terminally FLAG-tagged as shown in FIG. 6A so that display of the recombinant phage coat protein would be detectable (using commercial anti-FLAG antibody), even if the domains were not able to bind ligand. Several linkers were also tested for the presentation of suitable synthetic peptide ligands to find sequences that supported domain binding without exhibiting undue non-specific binding (data not shown). The expressed proteins also contained an ST2 secretion signal that is cleaved off and a C-terminal phage coat protein p3 (that is, fused to the C-terminus/residue 106 of *E. coli* ClpS) as shown in FIG. 6C. The WT ClpS expression protein used for Phage-displayed ClpS from *Escherichia coli* (*E. coli*) was able to bind its cognate ligand (immobilized Leucine) as shown in FIG. 6B, indicating that the ClpS domain was functionally displayed and hence suitable for use as a scaffold.

Library Construction

Combinatorial libraries of ClpS domain variants were generated using oligo-directed mutagenesis to introduce amino acid diversity into key positions (i.e. putative ligand determinants).

The ClpS libraries were used to gather extensive data on the sort of amino acid diversity that would be structurally tolerated at key positions forming (i.e. near or in) the ligand binding pocket with the goal of generating a highly functional library that exploits as much amino acid diversity as possible, while minimizing the number of library variants that destabilize or result in an unfolded scaffold.

Figure 7:
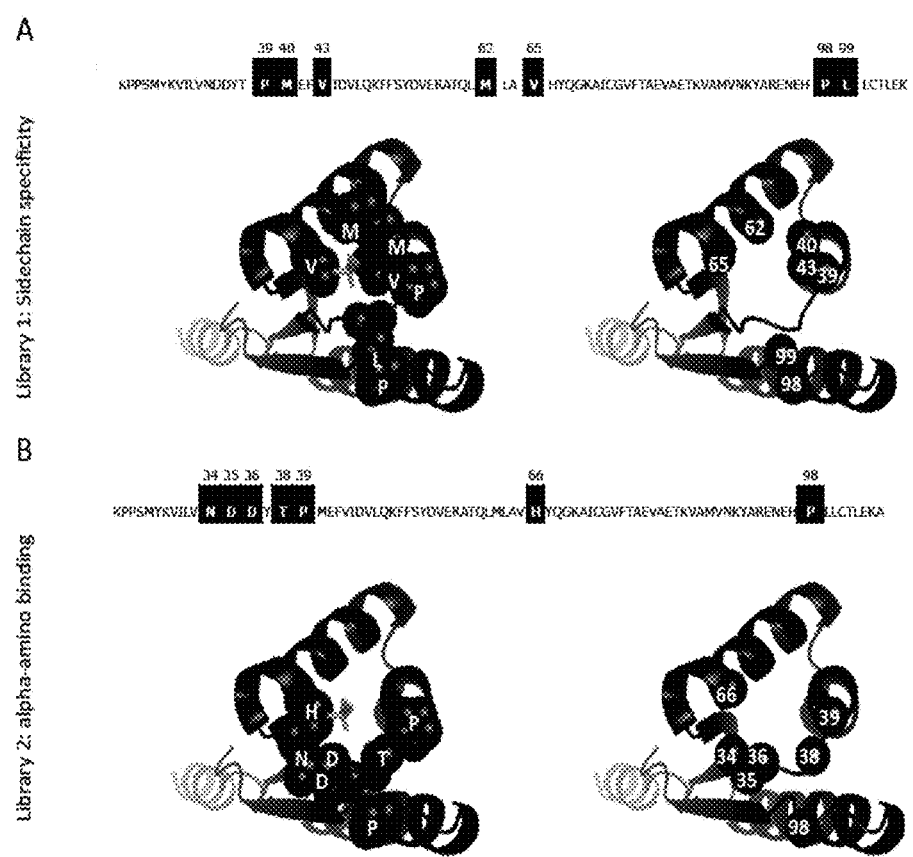
FIG. 7 shows the relative positions of the key residues hard randomized for the ClpS (SEQ ID NO: 22) phage display libraries for sidechain specificity (FIG. 7A) and alpha-amino binding (FIG. 7B).

Given that there are two components to N-terminal ligand recognition (specificity pocket residues, and alpha-amino recognition), two libraries were designed as shown in FIG. 7. In the first library, the specificity pocket residues were hard randomized to generate variants with all possible genetically encoded amino acids at the designated residues shown in FIG. 7A (corresponding to residue positions 17, 18, 21, 40, 43, 76 and 77 of the WT truncated ClpS polypeptide (SEQ ID NO: 1) shown as positions 39, 40, 43, 62, 65, 98 and 99 in FIG. 7A). In the second library, the residues responsible for alpha-amino recognition were hard randomized as shown in FIG. 7B (corresponding to residue positions 12, 13, 14, 16, 17, 44, and 76 of the WT truncated ClpS polypeptide (SEQ ID NO: 1) shown as positions 34, 35, 36, 38, 39, 66 and 98 in FIG. 7B).

Target Selection

The N-terminal FLAG tag was used to select for protease resistant domains expressed on the phage surface using an immobilized anti-FLAG antibody. Only domains that are reasonably well folded will escape degradation by host bacterial proteases during the phage amplification process. These domain were recovered and a large number were sequenced in order to determine a sense of the amino acid diversity that is structurally tolerated at each randomized position. The results of these structure selections indicate that the specificity pocket residues of ClpS are surprisingly tolerant to the full range of amino acid diversity.

For example, as seen in FIG. 8A, while the most frequently observed residue at position 99 is the same as the wildtype (Leu), followed by other aliphatic residues, polar and charged residues are also commonly observed at that position. Likewise, the alpha-amino recognition positions shown in FIG. 8B are also very tolerant for residue alterations.

Given the discovery that the specificity pocket library was functionally robust, selections against synthetic peptide ligands were carried out using this library. The specificity pocket library was selected against 20 biotinylated peptides, each with a different N-terminal residue atop a common leader sequence (X-SDGMFTAGSLIGK(biotin)) (SEQ ID NO: 4). The peptides were immobilized individually to the bottom wells of a microtiter plate. In order to recover highly selective binders, competitors were included in solution, i.e., non-biotinylated peptides with different N-terminal residues, during each round of panning against the immobilized ligands. The most stringent competition employed was to include eighteen peptides with the other N-terminal residues (excluding the immobilized residue and cysteine) at a concentration slightly higher than the reported dissociation constant of the wildtype ClpS:Leu-peptide interaction (Kd=4.8 uM; competitor concentration=10 µM). Consequently, ClpS mutant variants that prefer other residues in addition to the ligand 'bait' would bind those competing peptides in solution and simply be washed away. Only selective variants that bound to the immobilized target(s) were amplified during each subsequent round of selection.

In addition to the pooled competitor selection, two less stringent competition strategies were also performed: a) Leu- and Phe-peptides (both at 10 µM), in order to recover variants that prefer anything other than the wildtype ligands; and Gly-peptide (at 10 µM), in order to recover domains that have higher affinity for any N-terminus side chain rather than for no side chain. Additionally, selections without any competition were carried out, as a baseline for evaluating the effectiveness of the competition strategies and concentrations.

To evaluate the specificity and selectivity of individual clones, both wild-type ClpS and the selected variants' binding to each of the biotinylated peptides independently were tested. The same approach was also used to monitor the progress of the selections and to prioritize particular pools of phage for further investigation. The resulting specificity profile of the phage displaying wildtype ClpS is shown in Table 1. As expected, ClpS showed a clear preference for Leu, Tyr, Phe and, more weakly, Trp peptides.

TABLE 1

Phage displayed wild-type *E. coli* ClpS shows binding preferences for a panel of immobilized peptides consistent with published biophysical data and peptide profiling.

| N-terminal amino acid | ClpS Wt |
|---|---|
| A | −0.29 |
| C | −0.23 |
| D | −0.29 |
| E | −0.26 |
| F | 1.81 |
| G | −0.04 |
| H | −0.03 |
| I | −0.016 |
| K | 0.05 |
| M | −0.11 |
| N | −0.05 |
| P | −0.07 |
| Q | −0.18 |
| R | 0.13 |
| S | −0.01 |
| T | 0.01 |
| V | −0.09 |
| W | 0.77 |
| Y | 1.08 |
| L | 1.57 |
| N/A | −0.29 |
| N/A | −0.11 |

Promising single clones were picked from the selection pools and their specificity was evaluated using the same panel of biotinylated peptides and various amounts of phage supernatant. As shown in Table 2, probe variants exhibiting markedly different binding properties compared to the native ClpS protein were generated. In particular, ClpS Variant 1 bound specifically to tryptophan alone, a level of specificity which has not been reported before, and also gave a much stronger signal than wildtype ClpS, indicating it is more efficiently displayed and/or more stable than the wildtype sequence. Accordingly, Variant 1 represents a selective N-terminal amino acid capture probe for tryptophan useful for the sequencing methods described herein. Variant 1 also represents a useful scaffold for performing further generation and selection of variants with desirable properties for use as additional N-terminal amino acid capture probes.

In addition, Variant 2 was shown to have good selectivity for lysine. Variants 3 and 4 preferentially recognized glutamine and aspartic acid respectively, amino acids that are not recognized by wildtype ClpS. Accordingly, probes that exhibit (i) highly selective ligand binding (single N-terminal residue specificities), and (ii) different binding capabilities as compared to the wildtype ClpS scaffold can readily be generated using the methods described herein.

TABLE 2

Engineered ClpS variants shows differential binding to peptide ligand N-termini.

| | ClpS WT 10× | Variant 1 1× | Variant 2 5× | Variant 3 1× | Variant 4 1× |
|---|---|---|---|---|---|
| A | −0.29 | 0.018 | −0.049 | −0.015 | 0.009 |
| C | −0.23 | 0.066 | −0.059 | −0.005 | 0.021 |
| D | −0.29 | −0.017 | −0.07 | −0.003 | 0.91 |
| E | −0.26 | 0.032 | −0.087 | −0.023 | 0.033 |
| F | 1.81 | 0.083 | −0.207 | −0.006 | 0.035 |
| G | −0.04 | 0.028 | −0.135 | −0.006 | 0.011 |
| H | −0.03 | −0.001 | −0.113 | −0.031 | 0 |
| I | −0.16 | −0.023 | −0.079 | −0.027 | −0.022 |
| K | 0.05 | 0.129 | −0.201 | −0.007 | 0.01 |
| M | −0.11 | −0.003 | −0.072 | −0.017 | −0.003 |
| N | −0.05 | 0.052 | −0.063 | −0.011 | 0.002 |
| P | −0.07 | 0.062 | 0.153 | −0.039 | −0.022 |
| Q | −0.18 | 0.065 | −0.178 | 0.356 | −0.016 |
| R | 0.13 | 0.04 | 0.429 | −0.082 | −0.051 |
| S | −0.01 | −0.001 | −0.108 | 0.022 | 0.013 |
| T | 0.01 | −0.005 | −0.033 | −0.042 | −0.029 |
| V | −0.09 | 0.032 | −0.234 | −0.002 | −0.006 |
| W | 0.77 | 2.636 | −0.223 | −0.019 | −0.017 |
| Y | 1.08 | 0.045 | −0.235 | 0.006 | −0.001 |
| L | 1.57 | 0.069 | 1.609 | −0.031 | −0.006 |
| NA | −0.29 | 0.064 | −0.015 | 0.025 | 0.031 |
| NA | −0.11 | −0.023 | −0.052 | 0.014 | 0.016 |
| FLAG | — | — | — | — | — |
| | sub Fab | sub Fab | sub Fab | sub Fab | sub Fab |

Materials and Experimental Methods
Phage Screens

The selection and ELISA protocols are very similar. Briefly, each well of a 96-well Maxisorp plate was coated overnight at 4° C. with 100 µl of 10 µg/ml neutravidin in PBS, or 1:500 dilution of anti-FLAG antibody. Plates were washed three times with PBS+0.50% TWEEN-20 (PT) and blocked for 1 hour at room temperature with 200 ul of PBS+0.5% BSA (PB). Plates were washed again three times with PT. Stock solutions of biotinylated peptides (4 mg/ml in 100% DMSO) were diluted to 500 pM in PBS+5% DMSO. Dilute peptide solution was incubated on neutravidin-coated wells for 1 hour at room temperature, and then plates were washed three times with PT.

For selections, 100 ul of PEG-precipitated library phage, or pH adjusted phage supernatant from overnight culture, was added to appropriate wells and allowed to bind for 2 hours at 4° C. The plate was then washed six times with cold PT. Phage were eluted by addition of 100 ul of log-phase XL1 Blue culture OD600=0.4) directly to the selection plate and incubation for 30 minutes at 37 C with 200 rpm. Helper phage (M13K07) was then added to a final concentration of 1010 phage/ml and the selection plate was incubated for another 45 minutes at 37 C with 200 rpm. Finally, the cells were transferred to 1.3 ml of 2YT+carbenicillin (100 µg/ml)+kanamycin (25 µg/ml) in a deep well plate and grown overnight at 37° C. with 200 rpm. The following day, the cells were precipitated by 10 minute centrifugation at 3000×g at 4° C. The phage supernatant was then transferred to a clean deep well plate and the pH adjusted by addition of 10×PBS to a final concentration of 1×.

Enzyme-Linked Immunoassays

For the ELISA readouts, 100 µl of pH adjusted phage supernatant or polyethylene glycol (PEG) precipitated concentrated phage was added to appropriate wells and allowed to bind for 1 hour at 4° C. The plate was then washed three times with cold PT. anti-M13:HRP conjugated antibody was diluted 1:3000 in cold blocking buffer and 100 µl aliquotted to each well, for incubation at 4° C. for 15 minutes. The plate was then washed six times with cold PT. 90 µl of TMB detection substrate was added to each well and allowed to develop for approximately 5 minutes. The reaction was stopped by addition of 90 µl of 1M H3PO4 and the absorbance at A450 nm was read.

Example 5

ClpS Probe Labeling and Detection

In order to allow for the detection of N-terminal amino acid affinity capture probes bound to individual surface-immobilized polypeptides, the probes are optionally detectably labeled with a fluorescence-based marker. Accordingly, various methods of labeling the probes were investigated using FluoSpheres™ (FS) (Invitrogen), which comprise polystyrene shells encompassing core dye molecules. FluoSpheres™ with the same surface chemistry are available in a useful range of sizes (20 nm-1 µm diameter). In addition, FluoSpheres with a number of different dyes with varying emission spectra to generate discernible probes for multiplex analysis are available.

20 nm diameter FluoSpheres (FS20) with the Nile Red dye were selected to minimize the footprint of the peptide-bound labeled ClpS. However, if the fluorescence intensity is found to be inadequate for a single-molecule detection, a larger particle can also be used.

Two different (indirect and direct) conjugation schemes were used to attach fluorescent labels to ClpS proteins as shown in FIGS. 9 and 10. The first (indirect) labeling approach is based on the fact that the recombinant ClpS used for the present Experiments was expressed and isolated from E. coli as fusions with an N-terminal glutathione transferase (GST) domain, which strongly binds glutathione (GSH). Therefore, after the FluoSpheres are functionalized with GSH, mixing FS20 with the purified protein should effectively fluorescently label the ClpS probe through the GST-GSH interaction. Furthermore, since this conjugation approach involves an interaction with the GST rather than the amino acid-binding domain of ClpS, it is not expected to significantly interfere with the peptide-binding functionality of the probes.

Indirect Probe Labeling

Glutathione is a tripeptide of glutamine, cysteine and glycine, with cysteine in the central position. To prevent GSH immobilization from interfering with GST binding, GSH was attached to the FluoSpheres through thiol of the cystein residue using a long linker molecule (see Chen et al. *Effect of Linker for Immobilization of Glutathione on BSA-Assembled Controlled Pore Glass Beads.* Bull. Kor. Chem. Soc. 25 (2004) 1366-1370). Sulfo-LC-SPDP was selected as a suitable ~1.5 nm long heterofunctional linker molecule with thiol and amine-reactive ends. In order for this molecule to be used for GSH immobilization on FS20, the Fluosphere surface was first functionalized with amines. This was achieved by reacting FS20 with ethylenediamine in a process catalyzed by the 1-ethyl-3-(3-dimethylaminopropyl) carbodiimide (EDC) crosslinker, which forms an amide bond between the carboxylic acids and amines. Amine-functionalized FS20 (diaminated FS20-DA) was then reacted with Sulfo-LC-SPDP, leaving the thiol reactive end for further conjugation to the GSH. Once the FluoSpheres containing different dyes were functionalized with GSH, they were used to fluorescently label end-terminal amino acid binding ClpS proteins simply by mixing the two populations together. Probes directed to different N-terminal amino acids can also readily be labeled with a differentially colored dye, allowing for the use of multiplexing in probe detection.

Direct Probe Labeling

The second (direct) labeling approach involves direct covalent attachment of the fluorescent label to the probe. This is achieved by using EDC to form an amide bond between the carboxylic acids on FS20 surface, and the primary amines of the ClpS probe. This scheme is simpler than the first one, since it does not require Fluosphere™ functionalization with glutathione, however, the drawback is that the location of the reacting amine on the ClpS protein cannot be controlled. If the attachment preferentially takes place on the ClpS peptide-binding domain rather than the GST moiety, it might interfere with the primary function of ClpS protein to bind a terminal amino acid on a peptide.

Making Amine-Functionalized Fluo-Spheres 20 nm diameter FluoSpheres™ (FS20), purchased from Invitrogen, contained carboxylic acid functional groups on their surface. The synthetic scheme for adsorbing glutathione (GSH) onto their surface required the presence of amine groups instead. Amine functionalization of FS20 (FS20-DA) was performed by mixing FS20 and ethylene diamine (DA) in the presence of 1-ethyl-3-(3-dimethylaminopropyl) carbodiimide (EDC) crosslinker, which catalyzes the formation of a stable amide bond between a carboxylic acid and an amine.

The resulting FluoSpheres were evaluated by agarose gel electrophoresis by fluorescence imaging of the gel (data not shown). FS20 functionalized with carboxylic acids have a negative (−) surface charge, and therefore migrate in the direction of the cathode (+). When functionalized with amines, FS20-DA surface is expected to attain a more positive charge (negative carboxylic acids are replaced with positive amines). This should lead to a slower gel migration of FS20-DA than of FS20 in the (+) direction (assuming only a fraction of carboxyl groups get modified, so that overall surface charge is still negative; if majority or carboxylic acids are modified the net surface charge will be positive, leading to migration in the (−) direction). In agreement with these predictions, for FS20 reacted with dilution series of ethylene diamines, as the concentration of the diamine was increased, a larger number of carboxyl groups get replaced with amines, leading to a slower migration of the FluoSpheres™ on the gel. The results further demonstrated that only a portion of carboxylic acids reacts with diamines: even in the conditions of diamine saturation, FS20-DA still migrate in the direction of cathode, indicating net negative surface charge remains.

Amine-functionalization of FS20 was further confirmed by reacting FS20-DA with a FITC dye that reacts and forms bonds with amine groups (Fluorescein isothiocyanate isomer I). The expectation was that as the FS20-DA amine density increases when generated using higher concentrations of diamine, the quantities of dye associated with FS20-DA should increase as well. Since FITC emission peaks at a different wavelength than Nile Red, the presence of FITC dye could be detected by looking at the spectral emission profile of the samples. Excitation of FITC at 495 nm also excites Nile Red, so that normalization of FITC emission to the Nile Red emission peak accounts of the inter-sample variation of Fluosphere™ concentration. This allows for a quantitative comparison of FS20-DA surface-immobilized FITC dye. The results (data not shown) showed normalized FITC emission for the dye reacted with the FS20-DA dilution series samples. Moreover, the magnitude of FITC emission increased with higher concentrations of diamine reacted with FluoSpheres in a manner similar to the gel shifts.

Reacting Sulfo-LC-SPDP with the Amines on Fluosphere Surface

FS samples (1 M, 100 mM, and 10 mM) were reacted with Sulfo-LC-SPDP (referred to as SPDP) to form SPDP-functionalized FluoSpheres™ (FS20-SPDP). Following the reactions, FS20-SPDP were visualized using agarose gel electrophoresis. SPDP conjugation to amines on the surface of FluoSpheres blocks the (+) charge associated with the amines (SPDP is a neutral molecule and does not contribute to the charge). This leads to a more negative net surface charge, resulting in faster gel migration (effectively negating some of the charge difference between FS20 and FS20-DA). The SPDP-functionalized fluosphere samples were further probed with the amine-reactive FITC dye described above. Since some of the surface amine groups react with SPDP, FS20-SPDP should have fewer amine groups on their surface than FS20-DA. As a result, FITC dye association with FS20-SPDP should be lower as well. Indeed, this was the observed trend: after reaction with SPDP the different FS20-DA samples showed lower FITC dye binding (data not shown).

Conjugating SPDP-Functionalized FS20 to Glutathione (GSH)

In a new set of reactions, FS20 was sequentially reacted with ethylene diamine and SPDP. FS20-SPDP were then further conjugated to GSH (FS20-GSH). All of the samples were visualized on the agarose gel. As observed previously, amination of FluoSpheres leads to a slower migration of the particles on the gel. Introduction of SPDP groups blocks some of positive amine charges, and some of the fluosphere mobility is restored. Since GSH is negatively charged, FS20-GSH have higher net negative surface charge, and migrate faster towards the cathode than FS20-SPDP. Taken together, the data demonstrates the stepwise functionalization of carboxy-functionalized FS20 with glutathione.

Labeling ClpS Proteins with FS20 Through EDC-Catalyzed Reaction

ClpS proteins were conjugated directly to carboxyl-functionalized FS20 using EDC to crosslink carboxylic acids on FS20 with amines on ClpS. Three different concentrations of ClpS were used (2.8, 28, and 280 ClpS-to-FS20 ratio). In addition, controls without EDC were included to estimate non-specific binding between ClpS and FS20. All of the samples were visualized by gel electrophoresis: robust EDC-catalyzed crosslinking was observed, and the number of ClpS per FS20 (represented by the magnitude of the band shift) increased with increasing ClpS-to-FS20 ratio. Some residual adsorption of ClpS onto FS20 was observed in the absence of EDC crosslinker, but the EDC-based covalent association was much stronger.

These results demonstrate that recombinant ClpS can be fluorescently labeled directly with carboxyl-functionalized FluoSpheres in a simple one-step process.

Labeling of ClpS with FS20-GSH Through GSH-GST Interaction

FS20-GSH was incubated with the GST-tagged recombinant ClpS protein with a ClpS/FS20-GSH ratio of 250. The expectation was that the GSH immobilized on FluoSpheres would interact with the GST domains of ClpS, leading to the association between the proteins and FS20 molecules. The interaction between FS20-GSH and ClpS was probed using agarose gel electrophoresis followed by fluorescent imaging (data not shown). While the association between FS20-GSH and ClpS does take place, the data suggest that the degree of association is lower than for the EDC-catalyzed reaction.

Binding of Labeled ClpS Protein to Surface-Immobilized Peptides

Arg- and Leu-terminated biotinylated peptides were immobilized in NeutrAvidin-coated wells of a 96-well plate through biotin-NeutrAvidin interactions. Wells containing NeutrAvidin alone but no peptides were included as controls to estimate non-specific adsorption. Fluorescently labeled ClpS protein was then added to the wells and incubated to allow for the protein-peptide binding to occur. To exclude the possibility this might be due to non-specific binding, the wells were incubated with bound FS20-GSH-Clps in buffer containing reduced GSH. GSH present in excess was expected to compete for binding to the GST domain of recombinant proteins, thus releasing FS20-GSH into solution (observing fluorescence in solution should lead to lower background signal, since in the case of immobilized peptide the excitation laser focuses on the bottom of the well, thus maximizing the plate plastic's autofluorescence).

Figure 12:
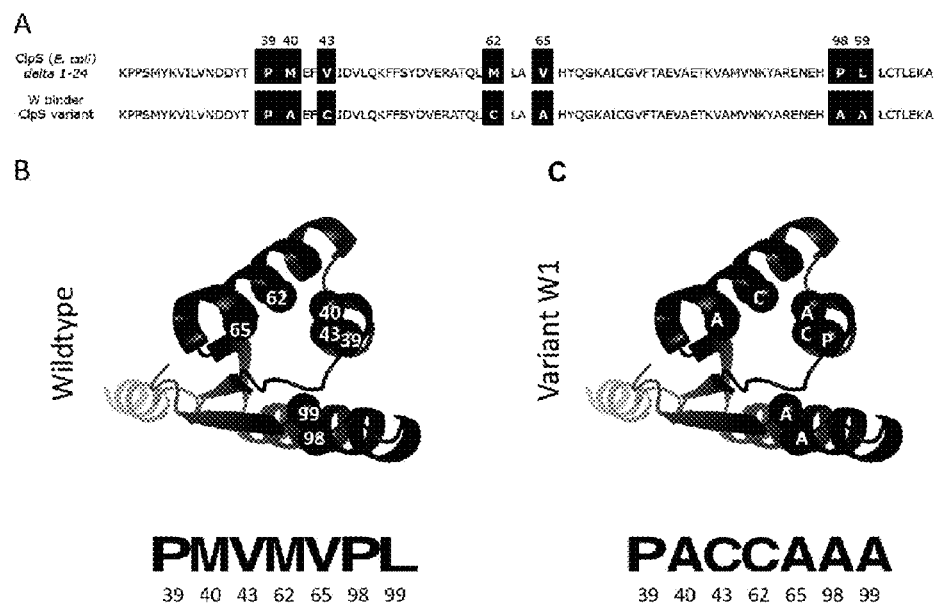
FIG. 12 shows the sequence of ClpS variant 1 that binds N-terminal tryptophan residues selectively.
Figure 13:
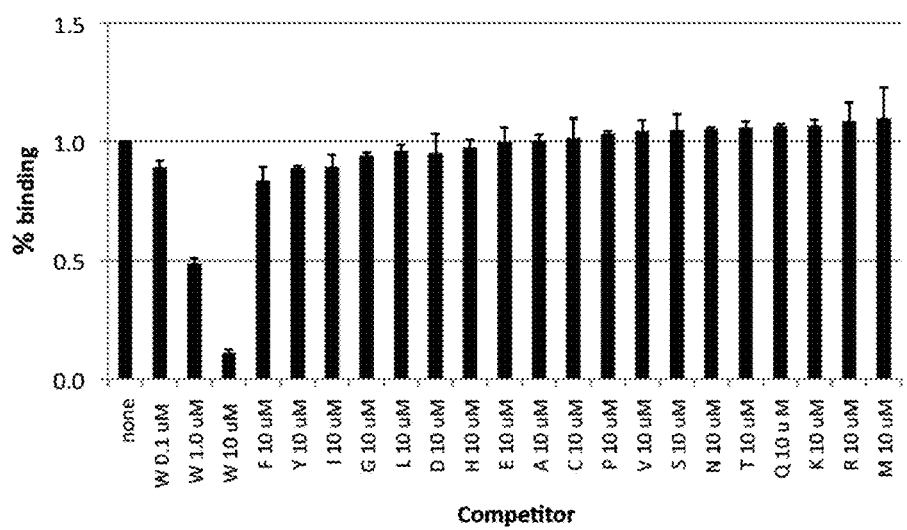
FIG. 13 shows results from competitive phage ELISA demonstrating that only Wpep is an effective competitor for binding ClpS Variant 1. Error bars represent 95% confidence intervals (n=2).

As shown in FIG. 12, ClpS labeled by FluoSpheres™ both through covalent conjugation or GST-GSH based interaction showed preferential binding for the Leu-terminated peptide. The magnitude of this interaction appeared stronger for the covalently labeled protein, which is consistent with observed lower ClpS-FluoSphere association with the GST-GSH labeling method.

Accordingly, ClpS proteins can be detectably labeled and used to identify the N-terminal residues on immobilized peptides. The results of these experiments, combined with the agarose gel data that indicates stable FluoSphere-protein association, demonstrate the advantages of the two labeling methods investigated in this pilot study: (i) direct EDC-catalyzed covalent conjugation leads to higher protein-to-FS20 loading ratios, which translates to stronger association (and hence signal) between FS20-ClpS and (plate) immobilized peptides; and (ii) indirect labeling through GST-GSH interaction.

Materials and Experimental Methods
Imaging Materials and Equipment 20 nm Nile Red (535/575) FluoSpheres™ were purchased from Invitrogen Canada Inc. (Burlington, ON). All other reagents were purchased from Sigma-Aldrich Canada Ltd. (Oakville, ON), except for Sulfo-LC-SPDP (X-Link Bioscience Inc., Freeport, Ill.). NAP-5 Sephadex desalting columns were purchased from GE Healthcare Life Sciences (Baie d'Urfe, QC). All agarose gels (1%) were run at 50 V. Fluorescence spectral measurements were performed using FluoroMax-3 spectrofluorometer (HORIBA Instruments Inc., Ann Arbor, Mich.).

Functionalizing FluoSpheres with Glutathione (GSH)

All of the reactions were performed in 0.1 M sodium phosphate buffer with 0.05% TWEEN (SPBT). The buffer was kept at pH 6.8 for EDC-based reactions, and adjusted to pH 7.2 for the SPDP conjugation. To make amine-functionalized FluoSpheres (FS20-DA), 100 μL of 20 nm Nile Red FluoSpheres (FS20) (2 mg/mL in SPBT) were mixed with 100 μL of 100 mM ethylenediamine dihidrochloride solution (in SPBT), then EDC (40 mg/mL in H2O, prepared immediately before use) was added to a final concentration of 2 mg/mL. The samples were incubated for 2 hours at room temperature, then purified by 2 rounds of desalting using NAP 5 SEPHADEX column. When generating FS20-DA using dilution series of diamine (1 M, 100 mM, 10 mM, 1 mM, 100 μM, or 10 μM, all in SPBT), 8 rounds of ultracentrifugation (300,000×g, 1 hour each) were used for purification.

To make SPDP-functionalized FS20 (FS20-SPDP), FS20-DA solution was adjusted to pH 7.2 by addition of NaOH, then 50 μL of Sulfo-LC-SPDP (5.2 mg/mL in H2O, prepared immediately before use) was added per 1 mL of FS20-DA suspension. The samples were incubated for 2 hours and purified by one round of desalting. When FS20-SPDP were generated from the diamine dilution series FS20-DA, 8 rounds of ultracentrifugation (300,000×g, 1 hour each) were used for purification.

To make GSH-functionalized FS20 (FS20-GSH), 50 μL of reduced L-Glutathione suspension in H2O (5.4 mg/mL, prepared immediately before use) was added per 1 mL of FS20-SPDP solution. The samples were incubated overnight, then purified by 3 rounds of desalting (to remove any remaining unbound GSH, Sulfo-LC-SPDP, diamine).

Reacting Amine and Sulfo-LC-SPDP Functionalized FS20 with Amine-Reactive Fluorescent FITC Dye 10 μL of 1 mM Fluorescein isothiocyanate isomer I dye solution (suspension in H2O) was added to 90 μL of FS20-DA or FS20-SPDP. The samples were incubated for 2 hours, and purified by 3 rounds of ultracentrifugation (300,000×g, 1 hour each) in the case of FS20-DA, and 5 rounds of purification for FS20-SPDP.

Labeling ClpS Protein Through GSH-GST Interaction

The labeling was achieved simply by mixing the suspensions of FS20-GSH and ClpS protein. No purification step was performed.

Labeling ClpS by EDC-Catalyzed Covalent Crosslinking

Equal volumes of the protein suspension (ClpS) and stock carboxylfunctionalized FS20 were mixed together. EDC (40 mg/mL in H2O, prepared immediately before use) was added to a final concentration of 2 mg/mL. The samples were incubated for 2 hours. No purification step was performed.

Binding of Labeled ClpS Protein to Surface-Immobilized Peptides

NeutrAvidin and anti-GST antibodies were immobilized in the wells of 96-well Nunc-Immuno™ Plates (100 μL of 10 μg/mL solution incubated for 2 hours at room temperature). Peptides (arginine and leucine terminated) conjugated to biotin were further adsorbed onto the NeutrAvidi-coated surface through biotin-NeutrAvidin interaction (50 pM per well). Labeled FS20-ClpS and FS20-GSH-ClpS were added at 10^12 particles/mL in SPBT buffer and incubated at 4° C. for 1 hour. The wells were then washed 6 times with SPBT, and fluorescence measurements were taken (dry well measurements). SPBT buffer with 10 mM GSH was then added to wells with FS20-GSH-ClpS, and incubated for 1 hour to release FS20-GSH into solution, following which the fluorescence measurements were taken. Fluorescent measurements were made using PHERAstar fluorescence plate reader (BMG Labtech, Offenburg, Germany).

Example 6

Characterization of the ClpS Variant 1 Trp-Binding N-Terminal Amino Acid Probe

The Trp-binding ClpS Variant 1 identified in Example 4 was isolated and sequenced in order to further characterize the properties of the N-terminal amino acid probe. The sequence of Variant 1 was determined to be as follows: KPPSMYKVILVNDDYTPAEF CIDVLQKFFSYDVERATQLCLA AHYQGKAICGVFTAEVA ETKVAMVNKYARENEH AALCTLEKA (SEQ ID NO:2)

Compared to the wildtype ClpS sequence, the Trp-binding ClpS Variant had mutations at positions 18, 21, 40, 43, 76 and 77 as shown in SEQ ID NO: 2. It is noted that the cystein variants at positions 21 and 40 may form a disulfide bond, which serves to stabilize the variant polypeptide while still allowing for N-terminal amino acid binding. FIG. 12 shows the sequence of wildtype ClpS (delta 1-34) as well as the Trp binding ClpS variant with key residues highlighted.

Competitive phage was also used to investigate the Trp binding ClpS variant and demonstrate that only Wpep is an effective competitor for binding. Phage bearing ClpS variant W1 were incubated with the indicated concentration of non-biotinylated peptide (X=N-terminal residue as indicated in FIG. 12, XSDGMFTAGSLI) and binding was allowed to reach equilibrium. Each phage pool was then briefly incubated in wells of a microtitre plate with Wpep ( WSDGMFTAGSLIGK(biotin)) immobilized on neutravidin. Non-binding phage were washed away, and retained phage were detected using an enzymatically-labeled antibody against the filamentous phage particle and an appropriate colorimetric substrate. The value for W1 binding to neutravidin alone was subtracted from the binding signal from every well to correct for non-specific binding. The ELISA values were then expressed as proportions, relative to the maximum ELISA signal in absence of competitor. Error bars represent 95% confidence intervals (n=2). As shown in FIG. 12, the concentration of Wpep competitor required to block 50% of variant W1 binding (inhibitory concentration 50 or IC50) is approximately 1 uM. Wpep competitor at 10 uM reduces binding to 11%. At that same concentration, peptides with other N-terminal residues are much less effective competitors (F, Y, I, G, L) or ineffective (all other natural residues), demonstrating ClpS variant W1's binding selectivity.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

All publications, patents and patent applications are herein incorporated by reference in their entirety to the same extent as if each individual publication, patent or patent application was specifically and individually indicated to be incorporated by reference in its entirety.

The invention claimed is:

1. A method of sequencing a polypeptide comprising:
   a. affixing the polypeptide to a substrate;
   b. contacting the polypeptide with a plurality of probes, wherein each probe comprises an affinity capture reagent that selectively binds to an N-terminal amino acid or a N-terminal amino acid derivative, and a fluorescent label, wherein the affinity capture reagent is a variant ClpS polypeptide comprising an amino acid sequence with at least 70% sequence identity to SEQ ID NO: 1 or 2;
   c. optically detecting the fluorescent label of the probe bound to the polypeptide molecule, thereby identifying the N-terminal amino acid of the polypeptide;
   d. cleaving the N-terminal amino acid or N-terminal amino acid derivative of the polypeptide; and
   e. repeating steps (b) to (d) to determine the sequence of at least a portion of the polypeptide.

2. The method of claim 1, wherein the polypeptide is a single polypeptide molecule.

3. The method of claim 1, wherein step b) further comprises derivatizing the N-terminal amino acid of the polypeptide prior to contacting the polypeptide with the plurality of probes.

4. The method of claim 1, wherein step a) comprises affixing the polypeptide to the substrate through a C'-terminal carboxyl group or a side chain functional group of the polypeptide.

5. The method of claim 1, wherein the polypeptide is covalently affixed to the substrate.

6. The method of any one of claim 1, wherein the substrate is optically transparent.

7. The method of claim 1, wherein the substrate comprises a plurality of spatially resolved attachment points and step a) comprises affixing the polypeptide to a spatially resolved attachment point.

8. The method of claim 1, wherein the plurality of probes comprises:
   a. one or more probes that selectively bind to an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;
   b. one or more probes that selectively bind to a post-translationally modified amino acid; or
   c. one or more probes that selectively bind to a derivative of a) or b).

9. The method of claim 1, wherein the variant ClpS polypeptide comprises one or more mutations at positions that correspond to residues 12, 13, 14, 16, 17, 18, 21, 40, 43, 44, 76 or 77 as set forth in SEQ ID NO: 1.

10. The method of claim 1, wherein step e) comprises cleaving the N-terminal amino acid or N-terminal amino acid derivative of the polypeptide using Edman degradation.

11. The method of claim 1, wherein the polypeptide is a partially or completely digested protein.

12. A method of sequencing a plurality of polypeptide molecules in a sample comprising:
   a. affixing the polypeptide molecules in the sample to a plurality of spatially resolved attachment points on a substrate;
   b. contacting the polypeptides with a plurality of probes, wherein each probe comprises an affinity capture reagent that selectively binds to an N-terminal amino acid or a N-terminal amino acid derivative and a fluorescent label, wherein the affinity capture reagent is a variant ClpS polypeptide comprising an amino acid sequence with at least 70% sequence identity to SEQ ID NO: 1 or 2;
   c. for a plurality of polypeptides molecule that are spatially resolved and affixed to the substrate, optically identifying the fluorescent label of the probe bound to each polypeptide;
   d. cleaving the N-terminal amino acid or N-terminal amino acid derivative of each of the polypeptides; and
   e. repeating steps b) to d) to determine the sequence of at least a portion of one or more of the plurality of polypeptide molecules that are spatially resolved and affixed to the substrate.

13. The method of claim 12, wherein the sample comprises a biological fluid, cell extract or tissue extract.

14. The method of claim 12, further comprising comparing the sequence of at least one polypeptide molecule determined in step e) to a reference protein sequence database.

15. The method of claim 12, further comprising comparing the sequences of each polypeptide determined in step e), grouping similar polypeptide sequences and counting the number of instances of each similar polypeptide sequence.

16. The method of claim 1, wherein the fluorescent label is a fluorescent moiety, color-coded nanoparticle or quantum dot.

17. The method of claim 12, wherein the fluorescent label is a fluorescent moiety, color-coded nanoparticle or quantum dot.

* * * * *

SEQUENCE LISTING

```
<160> NUMBER OF SEQ ID NOS: 22

<210> SEQ ID NO 1
<211> LENGTH: 84
<212> TYPE: PRT
<213> ORGANISM: Escherichia coli

<400> SEQUENCE: 1

Lys Pro Pro Ser Met Tyr Lys Val Ile Leu Val Asn Asp Asp Tyr Thr
1               5                   10                  15

Pro Met Glu Phe Val Ile Asp Val Leu Gln Lys Phe Phe Ser Tyr Asp
            20                  25                  30

Val Glu Arg Ala Thr Gln Leu Met Leu Ala Val His Tyr Gln Gly Lys
        35                  40                  45

Ala Ile Cys Gly Val Phe Thr Ala Glu Val Ala Glu Thr Lys Val Ala
    50                  55                  60

Met Val Asn Lys Tyr Ala Arg Glu Asn Glu His Pro Leu Leu Cys Thr
65                  70                  75                  80

Leu Glu Lys Ala

<210> SEQ ID NO 2
<211> LENGTH: 84
<212> TYPE: PRT
<213> ORGANISM: Artificial Sequence
<220> FEATURE:
<223> OTHER INFORMATION: Synthetic

<400> SEQUENCE: 2

Lys Pro Pro Ser Met Tyr Lys Val Ile Leu Val Asn Asp Asp Tyr Thr
1               5                   10                  15

Pro Ala Glu Phe Cys Ile Asp Val Leu Gln Lys Phe Phe Ser Tyr Asp
            20                  25                  30

Val Glu Arg Ala Thr Gln Leu Cys Leu Ala Ala His Tyr Gln Gly Lys
        35                  40                  45

Ala Ile Cys Gly Val Phe Thr Ala Glu Val Ala Glu Thr Lys Val Ala
    50                  55                  60
```

```
Met Val Asn Lys Tyr Ala Arg Glu Asn Glu His Ala Ala Leu Cys Thr
 65                  70                  75                  80

Leu Glu Lys Ala

<210> SEQ ID NO 3
<211> LENGTH: 277
<212> TYPE: PRT
<213> ORGANISM: Artificial Sequence
<220> FEATURE:
<223> OTHER INFORMATION: Synthetic

<400> SEQUENCE: 3

Met Lys Lys Asn Ile Ala Phe Leu Leu Ala Ser Met Phe Val Phe Ser
  1               5                  10                  15

Ile Ala Thr Asn Ala Tyr Ala Ser Met Gly Ser Asp Tyr Lys Asp Asp
                 20                  25                  30

Asp Asp Lys Gly Ser Lys Pro Pro Ser Met Tyr Lys Val Ile Leu Val
             35                  40                  45

Asn Asp Asp Tyr Thr Pro Met Glu Phe Val Ile Asp Val Leu Gln Lys
         50                  55                  60

Phe Phe Ser Tyr Asp Val Glu Arg Ala Thr Gln Leu Met Leu Ala Val
 65                  70                  75                  80

His Tyr Gln Gly Lys Ala Ile Cys Gly Val Phe Thr Ala Glu Val Ala
                 85                  90                  95

Glu Thr Lys Val Ala Met Val Asn Lys Tyr Ala Arg Glu Asn Glu His
            100                 105                 110

Pro Leu Leu Cys Thr Leu Glu Lys Ala Ser Arg Ser Gly Ser Gly Asp
        115                 120                 125

Phe Asp Tyr Glu Lys Met Ala Asn Ala Asn Lys Gly Ala Met Thr Glu
    130                 135                 140

Asn Ala Asp Glu Asn Ala Leu Gln Ser Asp Ala Lys Gly Lys Leu Asp
145                 150                 155                 160

Ser Val Ala Thr Asp Tyr Gly Ala Ala Ile Asp Gly Phe Ile Gly Asp
                165                 170                 175

Val Ser Gly Leu Ala Asn Gly Asn Gly Ala Thr Gly Asp Phe Ala Gly
                180                 185                 190

Ser Asn Ser Gln Met Ala Gln Val Gly Asp Gly Asp Asn Ser Pro Leu
            195                 200                 205

Met Asn Asn Phe Arg Gln Tyr Leu Pro Ser Leu Pro Gln Ser Val Glu
    210                 215                 220

Cys Arg Pro Phe Val Phe Ser Ala Gly Lys Pro Tyr Glu Phe Ser Ile
225                 230                 235                 240

Asp Cys Asp Lys Ile Asn Leu Phe Arg Gly Val Phe Ala Phe Leu Leu
                245                 250                 255

Tyr Val Ala Thr Phe Met Tyr Val Phe Ser Thr Phe Ala Asn Ile Leu
                260                 265                 270

Arg Asn Lys Glu Ser
        275

<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4
```

```
Ser Asp Gly Met Phe Thr Ala Gly Ser Leu Ile Gly Lys
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Tyr Phe Arg Thr Phe Arg Lys
1               5

<210> SEQ ID NO 6
<211> LENGTH: 18
<212> TYPE: PRT
<213> ORGANISM: Escherichia coli

<400> SEQUENCE: 6

Met Tyr Lys Val Ile Leu Val Asn Asp Asp Tyr Thr Pro Met Glu Phe
1               5                   10                  15

Val Ile

<210> SEQ ID NO 7
<211> LENGTH: 9
<212> TYPE: PRT
<213> ORGANISM: Escherichia coli

<400> SEQUENCE: 7

Leu Met Leu Ala Val His Tyr Gln Gly
1               5

<210> SEQ ID NO 8
<211> LENGTH: 18
<212> TYPE: PRT
<213> ORGANISM: Caulobacter crescentus

<400> SEQUENCE: 8

Leu Tyr Arg Val Leu Ile Leu Asn Asp Asp Tyr Thr Pro Met Glu Phe
1               5                   10                  15

Val Val

<210> SEQ ID NO 9
<211> LENGTH: 9
<212> TYPE: PRT
<213> ORGANISM: Caulobacter crescentus

<400> SEQUENCE: 9

Ile Met Leu His Val His Gln Asn Gly
1               5

<210> SEQ ID NO 10
<211> LENGTH: 18
<212> TYPE: PRT
<213> ORGANISM: Pseudomonas aeruginosa

<400> SEQUENCE: 10

Leu Tyr Lys Val Val Leu Phe Asn Asp Asp Tyr Thr Pro Met Asp Phe
1               5                   10                  15

Val Val

<210> SEQ ID NO 11
```

```
<211> LENGTH: 9
<212> TYPE: PRT
<213> ORGANISM: Pseudomonas aeruginosa

<400> SEQUENCE: 11

Ile Met Leu Thr Val His Thr Gln Gly
1               5

<210> SEQ ID NO 12
<211> LENGTH: 18
<212> TYPE: PRT
<213> ORGANISM: Mycobacterium tuberculosis

<400> SEQUENCE: 12

Ala Trp Val Thr Ile Val Trp Asp Asp Pro Val Asn Leu Met Ser Tyr
1               5                   10                  15

Val Thr

<210> SEQ ID NO 13
<211> LENGTH: 9
<212> TYPE: PRT
<213> ORGANISM: Mycobacterium tuberculosis

<400> SEQUENCE: 13

Leu Met Leu Gln Val His Asn Glu Gly
1               5

<210> SEQ ID NO 14
<211> LENGTH: 18
<212> TYPE: PRT
<213> ORGANISM: Synechococcus RS9916

<400> SEQUENCE: 14

Arg Tyr Lys Val Leu Leu His Asn Asp Pro Val Asn Ser Met Glu Tyr
1               5                   10                  15

Val Val

<210> SEQ ID NO 15
<211> LENGTH: 9
<212> TYPE: PRT
<213> ORGANISM: Synechococcus RS9916

<400> SEQUENCE: 15

Val Met Leu Glu Ala His Asn Ser Gly
1               5

<210> SEQ ID NO 16
<211> LENGTH: 18
<212> TYPE: PRT
<213> ORGANISM: Saccharomyces cerevisiae

<400> SEQUENCE: 16

Asn Tyr Thr Val Ile Ile Tyr Asn Asp Glu Tyr His Asn Tyr Ser Gln
1               5                   10                  15

Ala Thr

<210> SEQ ID NO 17
<211> LENGTH: 9
<212> TYPE: PRT
<213> ORGANISM: Saccharomyces cerevisiae

<400> SEQUENCE: 17

Leu Thr Ser Arg Ile Asp Gly Glu Arg
```

-continued

<210> SEQ ID NO 18
<211> LENGTH: 18
<212> TYPE: PRT
<213> ORGANISM: Homo sapiens

<400> SEQUENCE: 18

Arg Tyr Tyr Cys Val Leu Phe Asn Asp Glu His His Ser Tyr Asp His
1               5                   10                  15

Val Ile

<210> SEQ ID NO 19
<211> LENGTH: 9
<212> TYPE: PRT
<213> ORGANISM: Homo sapiens

<400> SEQUENCE: 19

His Thr Thr Ala Ile Asp Lys Glu Gly
1               5

<210> SEQ ID NO 20
<211> LENGTH: 18
<212> TYPE: PRT
<213> ORGANISM: Homo sapiens

<400> SEQUENCE: 20

Thr Tyr Tyr Cys Met Leu Phe Asn Asp Glu Val His Thr Tyr Glu Gln
1               5                   10                  15

Val Ile

<210> SEQ ID NO 21
<211> LENGTH: 9
<212> TYPE: PRT
<213> ORGANISM: Homo sapiens

<400> SEQUENCE: 21

Phe Ala Thr Thr Val Asp Arg Asp Gly
1               5

<210> SEQ ID NO 22
<211> LENGTH: 97
<212> TYPE: PRT
<213> ORGANISM: Escherichia coli

<400> SEQUENCE: 22

Gln Leu Ala Glu Glu Lys Val Arg Asp Ala Leu Lys Pro Pro Ser Met
1               5                   10                  15

Tyr Lys Val Ile Leu Val Asn Asp Asp Tyr Thr Pro Met Glu Phe Val
                20                  25                  30

Ile Asp Val Leu Gln Lys Phe Phe Ser Tyr Asp Val Glu Arg Ala Thr
            35                  40                  45

Gln Leu Met Leu Ala Val His Tyr Gln Gly Lys Ala Ile Cys Gly Val
        50                  55                  60

Phe Thr Ala Glu Val Ala Glu Thr Lys Val Ala Met Val Asn Lys Tyr
65                  70                  75                  80

Ala Arg Glu Asn Glu His Pro Leu Leu Cys Thr Leu Lys Ala Gly
                85                  90                  95

Ala